United States Patent
Tokko et al.

(10) Patent No.: US 11,510,581 B2
(45) Date of Patent: Nov. 29, 2022

(54) FLUID BLADDER, BLOOD PRESSURE MEASUREMENT CUFF, BLOOD PRESSURE MONITOR, AND BLOOD PRESSURE MEASUREMENT METHOD

(71) Applicant: OMRON HEALTHCARE Co., Ltd., Kyoto (JP)

(72) Inventors: Yoshihide Tokko, Kyoto (JP); Ryosuke Doi, Kyoto (JP); Hiroshi Koshimizu, Kyoto (JP); Kenji Ono, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 802 days.

(21) Appl. No.: 16/458,265

(22) Filed: Jul. 1, 2019

(65) Prior Publication Data

US 2019/0320917 A1 Oct. 24, 2019

Related U.S. Application Data

(60) Division of application No. 15/850,603, filed on Dec. 21, 2017, now Pat. No. 10,383,527, which is a
(Continued)

(30) Foreign Application Priority Data

Jun. 24, 2015 (JP) .............................. JP2015-126954

(51) Int. Cl.
*A61B 5/021* (2006.01)
*A61B 5/022* (2006.01)
(Continued)

(52) U.S. Cl.
CPC .......... *A61B 5/02141* (2013.01); *A61B 5/022* (2013.01); *A61B 5/02225* (2013.01);
(Continued)

(58) Field of Classification Search
None
See application file for complete search history.

(56) References Cited

U.S. PATENT DOCUMENTS 6,231,517 B1 * 5/2001 Forstner ............. A61B 5/02233
600/495
2001/0016692 A1 8/2001 Itonaga et al.
(Continued)

FOREIGN PATENT DOCUMENTS

| CN | 1785116 A | 6/2006 |
| CN | 1792320 A | 6/2006 |

(Continued)

OTHER PUBLICATIONS

International Search Report issued in PCT/JP2016/058834, dated Jun. 21, 2016 (5 pages).
(Continued)

*Primary Examiner* — Jacqueline Cheng
*Assistant Examiner* — Jairo H Portillo
(74) *Attorney, Agent, or Firm* — Osha Bergman Watanabe & Burton LLP

(57) ABSTRACT

A blood pressure measurement method includes wrapping a cuff around a site. The cuff includes: a first bladder that swells due to receiving fluid and is arranged at an outer surface of the site that corresponds to a first half surface where an artery is; and a second bladder that swells due to receiving fluid and is arranged at the outer circumferential surface of the measurement site that corresponds to a second half surface opposite to the first half surface. During inflation, the pressure of the second bladder is made larger than the first bladder by supplying more fluid such that the stroke amount by which the second fluid bladder swells is larger in the thickness direction. Then, the two bladders are inflated at equal rates. In the process of inflating, or in the process of
(Continued)

deflating at rates equal to each other after inflating, blood pressure is measured.

1 Claim, 20 Drawing Sheets

Related U.S. Application Data continuation of application No. PCT/JP2016/058834, filed on Mar. 18, 2016.

(51) Int. Cl.
    *A61B 5/00*     (2006.01)
    *A61B 5/0225*     (2006.01)
    *A61B 5/0235*     (2006.01)

(52) U.S. Cl.
    CPC ........ *A61B 5/02233* (2013.01); *A61B 5/6824* (2013.01); *A61B 5/0225* (2013.01); *A61B 5/0235* (2013.01)

(56) References Cited

U.S. PATENT DOCUMENTS

2004/0034308 A1     2/2004     Inoue et al.
2010/0024811 A1     2/2010     Henry et al.
2010/0268092 A1     10/2010     Kobayashi et al.
2012/0240377 A1     9/2012     Ashida

FOREIGN PATENT DOCUMENTS

| CN | 102688026 A | 9/2012 |
|---|---|---|
| EP | 1075846 A9 | 4/2001 |
| JP | H09-117419 A | 5/1997 |
| JP | 2003-024286 A | 1/2003 |
| JP | 2003-144398 A | 5/2003 |
| WO | 99/055400 A1 | 11/1999 |

OTHER PUBLICATIONS

Written Opinion issued in PCT/JP2016/058834, dated Jun. 21, 2016 (5 pages).
Decision to Grant a Patent issued in Japanese Application No. 2015-126954, dated Jun. 6, 2017 (6 pages).
Office Action issued in Chinese Application No. 201680025713.0, dated Sep. 18, 2018 (15 pages).
Office Action in counterpart Chinese Patent Application No. 201680025713.0, dated Mar. 15, 2019 (12 pages).

* cited by examiner

FLUID BLADDER, BLOOD PRESSURE MEASUREMENT CUFF, BLOOD PRESSURE MONITOR, AND BLOOD PRESSURE MEASUREMENT METHOD

TECHNICAL FIELD

One or more embodiments of the present invention relate to a fluid bladder, and more specifically relates to a fluid bladder that is provided in a blood pressure measurement cuff and is for compressing a measurement site.

Also, one or more embodiments of the present invention relate to a blood pressure measurement cuff, and more specifically relates to a blood pressure measurement cuff that is wrapped around and compresses a measurement site such as an upper arm or a wrist.

Also, one or more embodiments of the present invention relate to a blood pressure monitor including this kind of blood pressure measurement cuff.

Also, one or more embodiments of the present invention relate to a blood pressure measurement method for measuring blood pressure using a cuff.

BACKGROUND ART

Conventionally, as disclosed in Patent Document 1 (JP 2003-24286) for example, a blood pressure measurement cuff has been known which includes a first air bladder and a second air bladder composed of a material with higher elasticity than the first air bladder, which are overlaid between a band for wrapping around a wrist serving as a measurement site and a half surface on the palm side (the ulnar artery and radial artery side) of the wrist. With this cuff, the arteries are compressed by inflating the first air bladder as well as the second air bladder.

CITATION LIST

Patent Literature

Patent Document 1: JP 2003-24286A

SUMMARY OF INVENTION

According to analysis performed by the inventor, as shown in FIG. 26(A), when an air bladder 420 is significantly inflated in a state in which the air bladder 420 is arranged between a band 410 and a half surface 90a on a palm side of a wrist 90, a radial artery 90u and an ulnar artery 90v are pressed by the inflated air bladder 420 as indicated by arrows B1 and B2 in FIG. 26(B) and withdraw into the gap between a palmaris longus tendon 90i and a radius 90g and the gap between a flexor digitorum superficialis tendon 90j and an ulna 90h respectively (the reason for this is because the air bladder 420 whose outer side is constrained by the band 410 inflates mainly toward the soft tissue between the palmaris longus tendon 90i and the radius 90g and between the flexor digitorum superficialis tendon 90j and the ulna 90h, as indicated by the arrows C1 and C2). For this reason, an extra amount of pressure is required in order to press the arteries 90u and 90v, as a result of which the measured values for blood pressure tend to be higher than the true values.

In view of this, one or more embodiments of the present invention aim to provide a fluid bladder that is provided in a blood pressure measurement cuff, can bring the measured values for blood pressure closer to the true values, and can increase measurement accuracy.

Also, one or more embodiments of the present invention aim to provide a blood pressure measurement cuff that can bring the measured values for blood pressure closer to the true values and can increase measurement accuracy.

Also, one or more embodiments of the present invention aim to provide a blood pressure monitor including this kind of blood pressure measurement cuff.

Also, one or more embodiments of the present invention aim to provide a blood pressure measurement method according to which it is possible to bring the measured values for blood pressure closer to the true values and to increase measurement accuracy.

A fluid bladder according to one or more embodiments of the present invention is a fluid bladder that is to be provided on a band-shaped blood pressure measurement cuff to be attached by being wrapped around a substantially rod-shaped measurement site, and is for compressing the measurement site, including:

a first fluid bladder region that that swells due to receiving a supply of fluid from an outside supply source and is arranged at a portion of an outer circumferential surface of the measurement site that corresponds to a first half surface where an artery is, in a lengthwise direction of the cuff; and a second fluid bladder region that swells due to receiving a supply of fluid from the outside supply source and is arranged at a portion of the outer circumferential surface of the measurement site that corresponds to a second half surface opposite to the first half surface, in the lengthwise direction of the cuff, wherein a configuration is used in which during inflation for blood pressure measurement, the first fluid bladder region and the second fluid bladder region are inflated to the same pressure and a stroke amount by which the second fluid bladder region swells is larger in a thickness direction of the cuff than a stroke amount by which the first fluid bladder region swells.

In the present specification, the "lengthwise direction" of the cuff refers to the direction corresponding to the direction of wrapping the outer circumferential surface of the measurement site. Also, the "thickness direction" of the cuff refers to a direction corresponding to the direction orthogonal to the outer circumferential surface of the measurement site.

Also, "outside" means the outside with respect to the cuff.

Also, "stroke amount" means a distance of swelling or expansion in the thickness direction.

When the blood pressure measurement cuff including the fluid bladder according to one or more embodiments of the present invention is attached by being wrapped around the measurement site, the first fluid bladder region corresponds to the first half surface, which is where the arteries exist, of the outer circumferential surface of the measurement site, and the second fluid bladder region corresponds to the second half surface, which is opposite to the first half surface, of the outer circumferential surface of the measurement site. During inflation for blood pressure measurement, the first fluid bladder region swells due to receiving a supply of fluid from an outside supply source. The second fluid bladder region also swells due to receiving a supply of fluid from the supply source. Here, with the fluid bladder, a configuration is used in which the first fluid bladder region and the second fluid bladder region are inflated to the same pressure and the stroke amount by which the second fluid bladder region expands is larger in the thickness direction of the cuff than the stroke amount by which the first fluid bladder region swells. Accordingly, when the first fluid bladder region and the second fluid bladder region are inflated to a certain pressure (the same pressure), the stroke amount by which the second fluid bladder region swells is larger in the thickness direction than the stroke amount by which the first fluid bladder region swells. Conversely, the first fluid bladder region swells less compared to the case where the second fluid bladder region does not exist and the case where the stroke amount by which the second fluid bladder region swells is less than or equal to the stroke amount by which the first fluid bladder region swells. Accordingly, the distance by which the arteries that exist at the measurement site withdraw due to being pressed by the first fluid bladder region decreases and the extra inflation amount for pressing the arteries decreases. As a result, the measured values for the blood pressure measured by inflating the fluid bladder can be brought closer to the true values, and the measurement accuracy can be increased. Also, during inflation for blood pressure measurement, in order to control the cuff pressure, it is sufficient that the control unit mounted in the blood pressure monitor main body, for example, controls the supply source so as to perform supply of the fluid to the first and second fluid bladder regions and discharge of the fluid from the first and second fluid bladder regions. Accordingly, control of the cuff pressure is simplified compared to the case where an element that expands or swells due to a different type of action than the fluid bladder, such as an actuator, for example, is included as the expansion region corresponding to the second half surface instead of the second fluid bladder region.

With a fluid bladder of an embodiment, the first fluid bladder region and the second fluid bladder region are in communication.

With the fluid bladder of this embodiment, since the first fluid bladder region and the second fluid bladder region are in communication, the first fluid bladder region and the second fluid bladder region can be inflated to the same pressure during inflation for blood pressure measurement.

With a fluid bladder of an embodiment, the first fluid bladder region is a portion of a parent bladder that extends in the lengthwise direction, the portion corresponding to the first half surface, and the second fluid bladder region is formed by overlaying a child bladder in a thickness direction on a portion of the parent bladder corresponding to the second half surface, and the fluid can flow between the parent bladder and the child bladder.

Here, "parent bladder" and "child bladder" are terms used for the sake of convenience to distinguish between the two bladders.

With the fluid bladder of this embodiment, during inflation for blood pressure measurement, when the first fluid bladder region and the second fluid bladder region are inflated to a certain pressure (the same pressure), the first fluid bladder region swells by a certain stroke amount in the thickness direction. At this time, the stroke amount of the first fluid bladder region is suppressed to a level corresponding to the parent bladder (one bladder). On the other hand, in the second fluid bladder region, the child bladder is overlaid on the parent bladder in the thickness direction. Accordingly, when the second fluid bladder region swells in the thickness direction, the stroke amount of the second fluid bladder region increases to a level corresponding to the parent bladder and the child bladder (at least two bladders). As a result, the stroke amount of the second fluid bladder region is larger than the stroke amount of the first fluid bladder region in the thickness direction. With the fluid bladder of this embodiment, the second fluid bladder region can be configured easily and inexpensively.

With a fluid bladder of an embodiment, a dimension in a width direction of the second fluid bladder region is set to be larger than a dimension in a width direction of the first fluid bladder region.

Here, "width direction" refers to a direction orthogonal to the lengthwise direction and the thickness direction. In the state in which the blood pressure measurement cuff including the fluid bladder is attached to the measurement site, the width direction corresponds to the direction along the arteries passing through the measurement site.

With the fluid bladder of this embodiment, during inflation for blood pressure measurement, the first fluid bladder region and the second fluid bladder region are inflated to the same pressure and swell. Here, the cross sections of the fluid bladder regions approach a circular shape as they swell, and if the width direction dimension of the fluid bladder region is large, the stroke amount in the thickness direction of the fluid bladder region increases accordingly. Accordingly, the second fluid bladder region swells by the stroke amount, which is larger in the thickness direction than the stroke amount of the first fluid bladder region. With the fluid bladder of this embodiment, the second fluid bladder region serving as the expansion region can be configured easily and inexpensively.

With a fluid bladder of an embodiment, in the second fluid bladder region, a pair of sheets that form the second fluid bladder region face each other in the thickness direction and edge portions in the width direction of the pair of sheets are welded or adhered in a state of being overlaid facing mutually opposite directions.

With the fluid bladder of this embodiment, during inflation for blood pressure measurement, when the first fluid bladder region and the second fluid bladder region are inflated to a certain pressure (the same pressure), the first fluid bladder region swells by a certain stroke amount in the thickness direction. Here, in the second fluid bladder region, a pair of sheets that form the second fluid bladder region face each other in the thickness direction and edge portions in the width direction of the pair of sheets are welded or adhered in a state of being overlaid facing mutually opposite directions. Accordingly, when the second fluid bladder region swells in the thickness direction, unlike the case where the edge portions of the pair of sheets are overlaid facing outward, there is no need to bend in order to open and no restriction occurs due to the inflexibility (stiffness) of the sheet material. As a result, the stroke amount in the thickness direction of the second fluid bladder region further increases. Accordingly, the measurement accuracy can be further increased. With the fluid bladder of this embodiment, the second fluid bladder region can be configured easily and inexpensively.

With a fluid bladder of an embodiment, a side portion of the second fluid bladder region is bellows-shaped or folded in a zig-zag shape in a cross-sectional view along the lengthwise direction in its natural state.

With the fluid bladder of this embodiment, during inflation for blood pressure measurement, when the first fluid bladder region and the second fluid bladder region are inflated to a certain pressure (the same pressure), the first fluid bladder region swells by a certain stroke amount in the thickness direction. At this time, the stroke amount of the first fluid bladder region is suppressed according to the amount by which the side portion stretches. On the other hand, a side portion of the second fluid bladder region is bellows-shaped or folded in a zig-zag shape in a cross-sectional view along the lengthwise direction in its natural state. Accordingly, when the second fluid bladder region swells in the thickness direction, the side portion that is bellows-shaped in its natural state or is folded in a zig-zag shape stretches. As a result, the stroke amount in the thickness direction of the second fluid bladder region further increases. Accordingly, the measurement accuracy can be further increased. With the fluid bladder of this embodiment, the second fluid bladder region can be configured easily and inexpensively.

With a fluid bladder of an embodiment, a thickness of the side portion of the second fluid bladder is thinner than a thickness of a sheet portion on a side away from the measurement site that forms the second fluid bladder region.

With the fluid bladder of this embodiment, during inflation for blood pressure measurement, when the first fluid bladder region and the second fluid bladder region are inflated to a certain pressure (the same pressure), the first fluid bladder region swells by a certain stroke amount in the thickness direction. Here, a thickness of the side portion of the second fluid bladder is thinner than a thickness of a sheet portion on a side away from the measurement site that forms the second fluid bladder region. Accordingly, when the second fluid bladder region swells in the thickness direction, the side portion of the second fluid bladder region is easier to stretch. As a result, the stroke amount in the thickness direction of the second fluid bladder region further increases. With the fluid bladder of this embodiment, the second fluid bladder region can be configured easily and inexpensively.

With a fluid bladder of an embodiment, a hardness of the side portion of the second fluid bladder is smaller than a hardness of a sheet portion on a side away from the measurement site that forms the second fluid bladder region.

With the fluid bladder of this embodiment, during inflation for blood pressure measurement, when the first fluid bladder region and the second fluid bladder region are inflated to a certain pressure (the same pressure), the first fluid bladder region swells by a certain stroke amount in the thickness direction. Here, a hardness of the side portion of the second fluid bladder is smaller than a hardness of a sheet portion on a side away from the measurement site that forms the second fluid bladder region. Accordingly, when the second fluid bladder region swells in the thickness direction, the side portion of the second fluid bladder region is easier to stretch. As a result, the stroke amount in the thickness direction of the second fluid bladder region further increases. With the fluid bladder of this embodiment, the second fluid bladder region can be configured easily and inexpensively.

According to another aspect, a blood pressure measurement cuff according to one or more embodiments of the present invention is a band-shaped blood pressure measurement cuff that is attached by being wrapped around a substantially rod-shaped measurement site, and includes the above-described fluid bladder.

With the blood pressure measurement cuff according to one or more embodiments of the present invention, because of the fluid bladder, the measured values for the blood pressure can be brought closer to the true values, and the measurement accuracy can be increased.

According to another aspect, a blood pressure monitor according to one or more embodiments of the present invention is a blood pressure monitor that includes the above-described blood pressure measurement cuff and a main body that includes an element for blood pressure measurement.

With the blood pressure monitor according to one or more embodiments of the present invention, because of the cuff, it is possible to bring the measured values for blood pressure closer to the true values and to increase measurement accuracy.

Furthermore, in another aspect, a blood pressure measurement method according to one or more embodiments of the present invention is a blood pressure measurement method including attaching a band-shaped measurement cuff such that it wraps around a substantially rod-shaped measurement site, wherein the cuff includes:

a first fluid bladder that swells due to receiving a supply of fluid and is arranged at a portion of an outer circumferential surface of the measurement site that corresponds to a first half surface where an artery is, in a lengthwise direction of the cuff, and a second fluid bladder that swells due to receiving a supply of fluid and is arranged at a portion of the outer circumferential surface of the measurement site that corresponds to a second half surface opposite to the first half surface, in a lengthwise direction of the cuff, during inflation for blood pressure measurement, the pressure of the second fluid bladder is made larger than the pressure of the first fluid bladder by supplying more fluid to the second fluid bladder than to the first fluid bladder such that the stroke amount by which the second fluid bladder swells is larger in the thickness direction of the cuff than the stroke amount by which the first fluid bladder swells, and after the stroke amount by which the second fluid bladder swells is made larger in the thickness direction than the stroke amount by which the first fluid bladder swells, the first fluid bladder and the second fluid bladder are inflated at pressure increase rates that are substantially equal to each other, and in the process of inflating, or in the process of deflating at pressure reduction rates that are equal to each other after the process of inflating, blood pressure measurement is performed.

With the blood pressure measurement method according to one or more embodiments of the present invention, the cuff is attached by being wrapped around the measurement site, and during inflation for blood pressure measurement, the pressure of the second fluid bladder is made larger by supplying a larger amount of fluid to the second fluid bladder than to the first fluid bladder such that the stroke amount by which the second fluid bladder swells is larger in the thickness direction of the cuff than the stroke amount by which the first fluid bladder swells. Thereafter, the first fluid bladder and the second fluid bladder are inflated at pressure increase rates that are substantially equal to each other, and in the process of inflating, or in the process of deflating at pressure reduction rates that are equal to each other after the process of inflating, blood pressure measurement is performed. Accordingly, the amount by which the arteries at the measurement site move due to being pushed by the first fluid bladder decreases, and the extra inflation amount of the first fluid bladder for pressing the arteries decreases. As a result, the measured values for blood pressure measured through inflation using the first fluid bladder can be brought closer to the true values and measurement accuracy can be increased.

Advantageous Effects of the Invention

As is evident from the above description, according to the fluid bladder, the blood pressure measurement cuff, the blood pressure monitor, and the blood pressure measurement method, the measured values for blood pressure can be brought closer to the true values and the measurement accuracy can be increased.

DESCRIPTION OF EMBODIMENTS

Hereinafter, embodiments of the present invention will be described in detail with reference to the drawings.

First Embodiment

Figure 1:
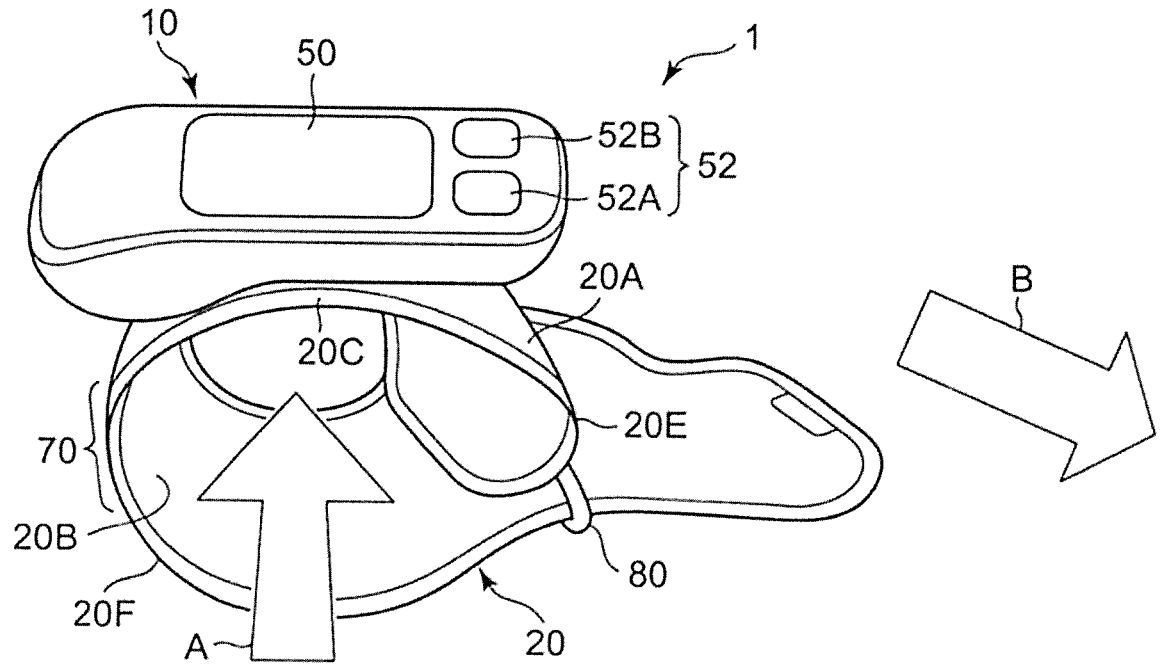
FIG. 1 is a schematic view showing an exterior of a blood pressure monitor that includes a blood pressure measurement cuff according to an embodiment of the present invention.

FIG. 1 shows an exterior of a blood pressure monitor (indicated by reference numeral 1 overall) of an embodiment of the present invention. The blood pressure monitor 1 mainly includes a blood pressure measurement cuff 20 that is wrapped around a wrist 90 (e.g., see FIG. 5) serving as a rod-shaped measurement site, and a main body 10 that is integrally attached to the cuff 20 and has elements for blood pressure measurement built in.

Figure 5:
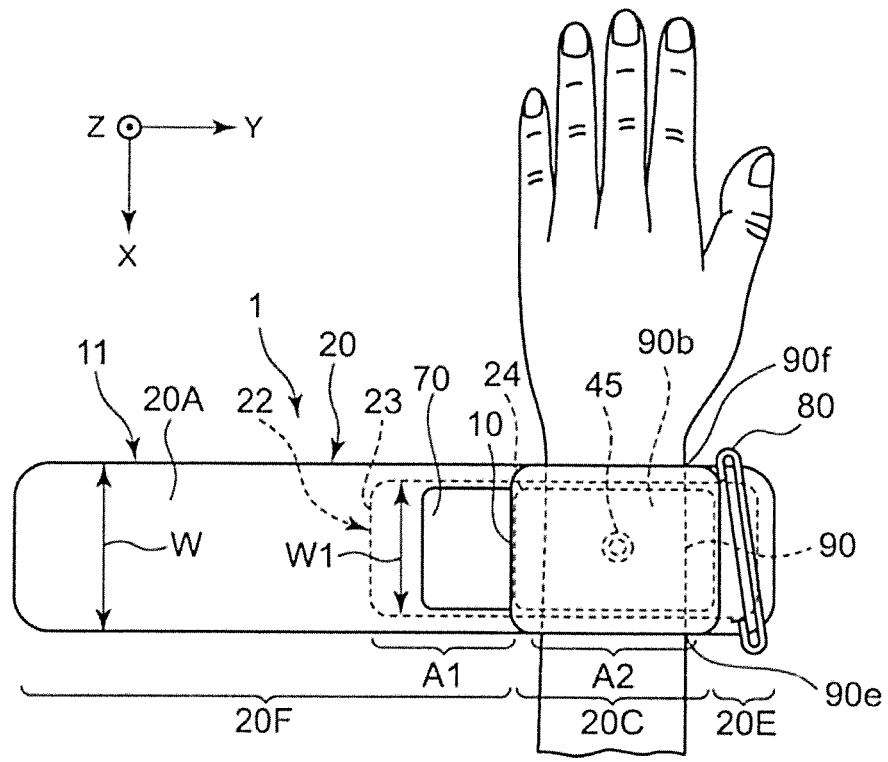
FIG. 5 is a diagram schematically showing a planar layout when the blood pressure monitor is viewed from a side on which a main body is provided in a state in which a cuff is unfolded.
Figure 6:
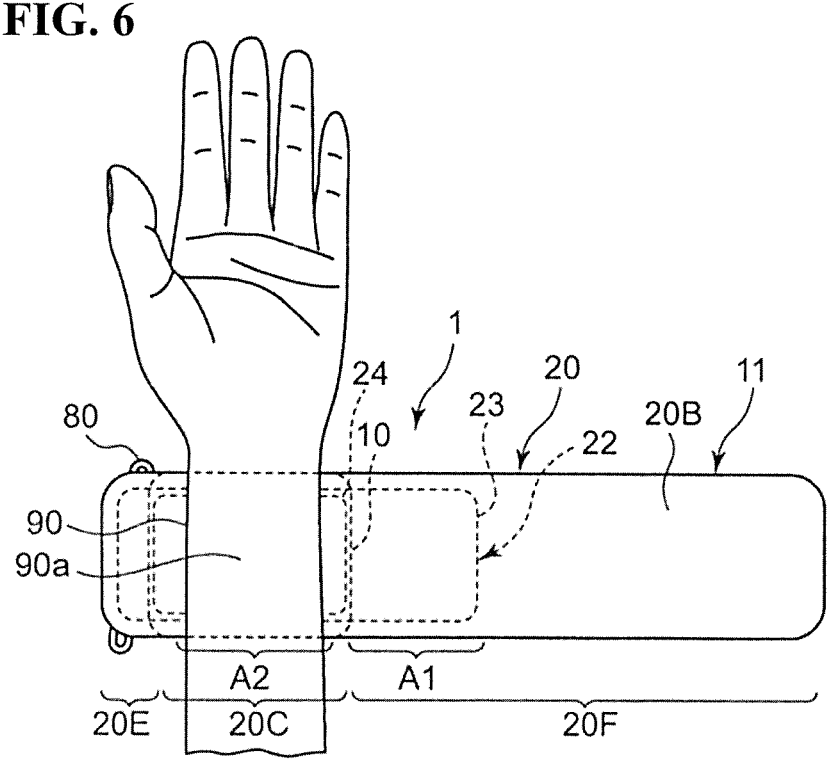
FIG. 6 is a diagram showing a planar layout when the blood pressure monitor is viewed from a side opposite to that in FIG. 5 in a state in which the cuff is unfolded.

FIG. 5 schematically shows a planar layout when the blood pressure monitor 1 is viewed from a side (corresponds to the outer circumferential side shown in FIG. 1) on which the main body 10 is provided, in a state in which the cuff 20 is unrolled. Also, FIG. 6 schematically shows a planar layout when the blood pressure monitor 1 is viewed from a side (corresponds to the inner circumferential side shown in FIG. 1) opposite to that shown in FIG. 5, in a state in which the cuff 20 is unrolled. Note that FIG. 5 also shows an orthogonal coordinate system XYZ in order to facilitate comprehension (the same follows in FIGS. 7, 9, 10(C), 11(C), 12, 13, 18, 19, and 20, which will be described later). FIGS. 5 and 6 also show the wrist 90 serving as the measurement site (the same follows in FIGS. 7, 9, 10(C), 11(C), 18, 19, and 21).

As can be understood from FIGS. 5 and 6, the cuff 20 is formed as a bladder-shaped band-shaped member 11 by sewing an outer cloth 20A and an inner cloth 20B along their edges. In order to make it easier to compress the measurement site, the inner cloth 20B has a large elasticity and the outer cloth 20A is set to be substantially non-elastic (or to have a smaller elasticity compared to the inner cloth 20B).

Along the lengthwise direction Y (corresponds to the circumferential direction in FIG. 1) of the cuff 20, the cuff 20 includes a second portion 20C that conforms to the main body 10, a first portion 20E that extends from the second portion 20C to one side (the right side in FIG. 5), and a third portion 20F that extends from the second portion 20C to the other side (the left side in FIG. 5). For example, the dimension in the lengthwise direction Y of the cuff 20 is within the range of about 300 mm to 400 mm, and a dimension W in the width direction X is set to be within the range of 30 mm to 60 mm.

A ring 80 that has a substantially oval shape is attached to the outer circumferential surface of the first portion 20E. The lengthwise direction of the ring 80 intersects with the lengthwise direction of the cuff 20. The dimension in the lengthwise direction of the ring 80 is set to be slightly larger than the width direction dimension W of the cuff 20 such that the cuff 20 (in particular, the third portion 20F) can easily pass therethrough. The reason why the ring 80 intersects with an inclination from the upper left to the lower right in FIG. 5 is because it is envisioned that the cuff 20 is attached by being wrapped around the wrist 90 in a state in which the elbow side (thick side) 90e of the wrist 90 is located below and the hand side (thin side) 90f of the wrist 90 is located above, as shown in FIGS. 5 and 6.

A planar fastener 70 is attached to the surface of the portion of the third portion 20F of the cuff 20 that is nearest to the main body 10. In this example, the planar fastener 70 includes many minute hooks (not shown) on its surface. The outer circumferential surface of the third portion 20F excluding the nearest portion (planar fastener 70) has many minute loops (not shown) that engage with the hooks.

An air bladder 22 serving as a fluid bladder for compressing the wrist 90 is contained in the cuff 20 spanning from the first portion 20E to the third portion 20F.

Figure 7:
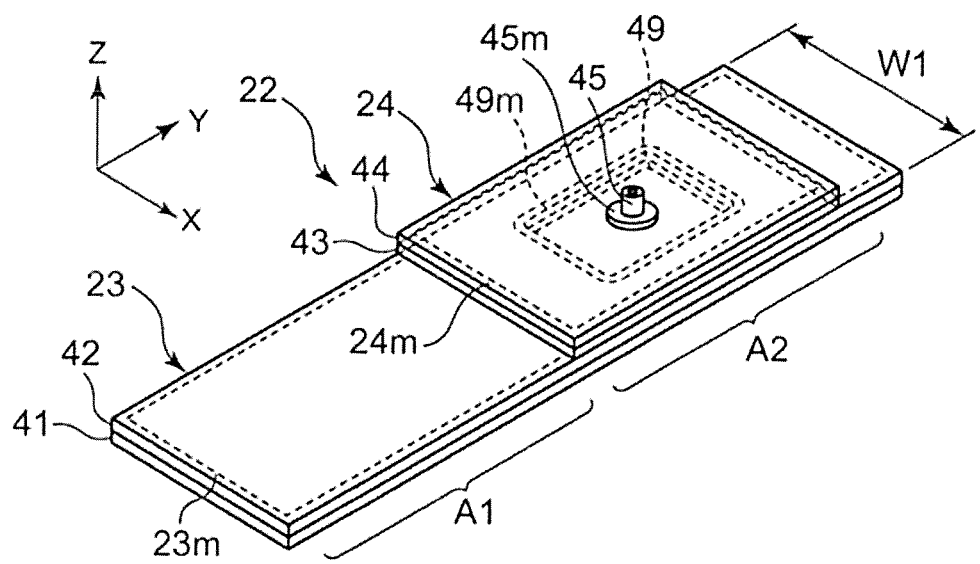
FIG. 7 is a schematic diagram showing an exterior of an air bladder serving as a fluid bladder contained in the cuff.

FIG. 7 shows a perspective view of the exterior of the air bladder 22. The width direction (X direction) of the air bladder 22 corresponds to the width direction of the cuff 20, or in other words, the direction along the arteries that pass through the wrist 90. The lengthwise direction (Y direction) and width direction (Z direction) of the air bladder 22 correspond to the lengthwise direction and the thickness direction of the cuff 20 respectively.

The air bladder 22 includes a parent bladder 23 that is arranged on the side (corresponds to the inner circumferential side shown in FIG. 1) near the wrist 90 serving as the measurement site, and a child bladder 24 that is arranged on a side (corresponds to the outer circumferential side shown in FIG. 1) away from the wrist 90. The parent bladder 23 is composed of two rectangular sheets 41 and 42 that have the same dimensions, are approximately flat, and are elongated in the lengthwise direction Y. The child bladder 24 is composed of two rectangular sheets 43 and 44 that have the same dimensions and are overlaid in the thickness direction Z in a region corresponding to a portion of the parent bladder 23 in the lengthwise direction Y. The dimensions W1 of the sheets 41, 42, 43, and 44 match in the width direction X. The parent bladder 23 and the child bladder 24 are configured such that air serving as a fluid can flow through a through hole 49. An approximately cylindrical nipple 45 for receiving a supply of air from an outside supply source (a later-described pump 32) and discharging air from inside of the air bladder 22 is attached to a sheet 44 on the upper side of the child bladder 24 so as to face the through hole 49 (the portion of the sheet 44 that corresponds to the inner radius of the nipple 45 penetrates therethrough such that the air can flow; this is referred to simply as "the nipple 45 being attached" as appropriate). For example, the dimension in the lengthwise direction Y of the air bladder 22 is set to be approximately half of the dimension in the lengthwise direction Y of the cuff 20. Also, the dimension W1 in the width direction X of the air bladder 22 is set to be about 5 mm smaller than the dimension W in the width direction of the cuff 20. The material of the sheets 41, 42, 43, and 44 is polyurethane resin in this example.

Here, the portion (included in the third portion 20F) corresponding to the half surface (first half surface of the outer circumferential surface of the wrist 90, where the ulnar artery and the radial artery exist) 90a on the palm side of the air bladder 22 that extends in the lengthwise direction Y will be referred to as "first fluid bladder region A1". On the other hand, the portion (approximately corresponds to the second portion 20C) of the air bladder 22 in which the child bladder 24 is arranged, and which corresponds to the half surface (second half surface opposite to the half surface 90a on the palm side 90a) of the outer circumferential surface of the wrist 90) 90b on the back side will be referred to as "second fluid bladder region A2".

Figure 9:
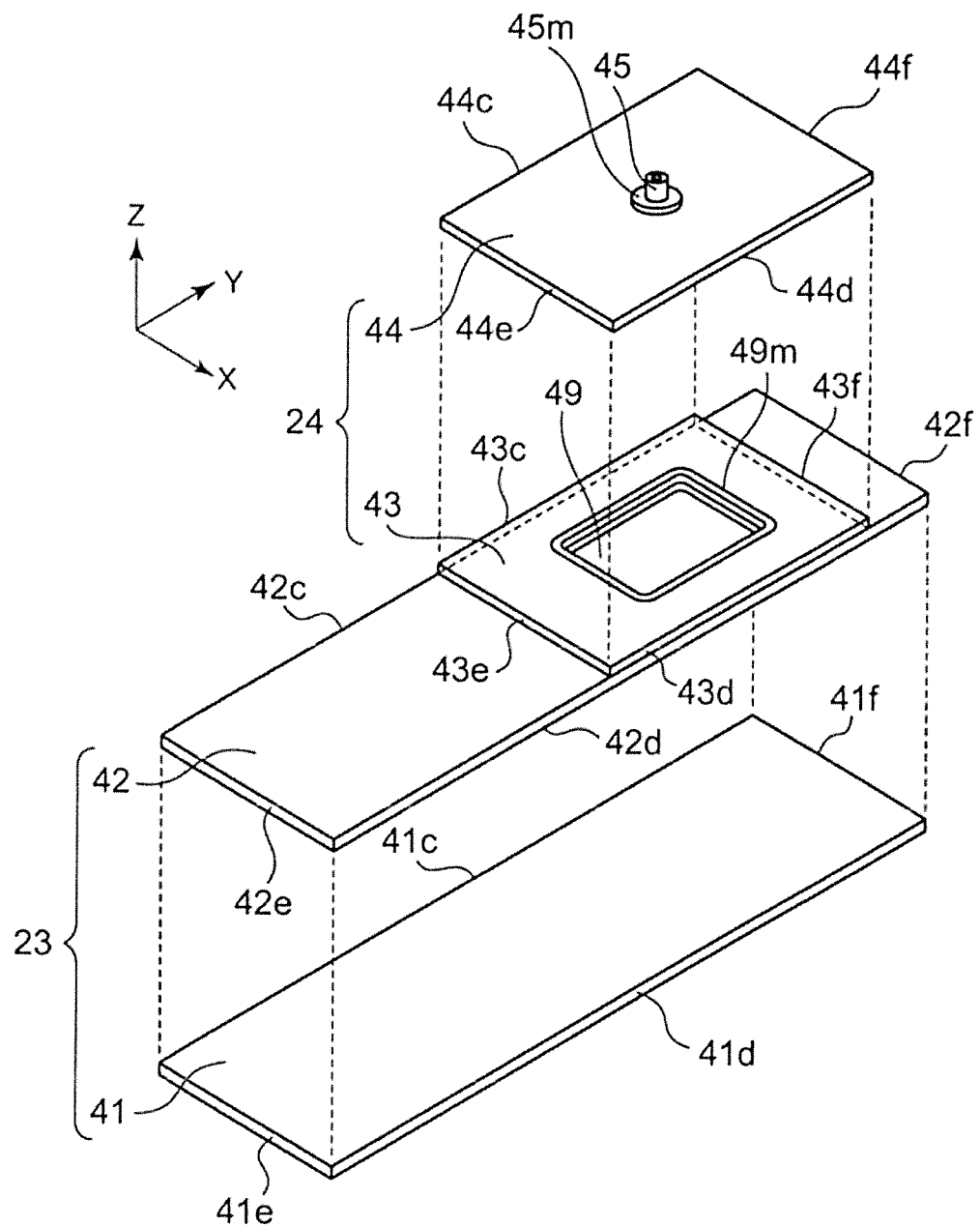
FIG. 9 is a diagram for illustrating a manufacturing step of manufacturing the air bladder shown in FIG. 7.

In the case of producing the air bladder 22, two approximately flat sheets 41 and 42 for forming the parent bladder 23 and two approximately flat sheets 43 and 44 for forming the child bladder 24 are prepared, as shown in FIG. 9, for example. For example, the thicknesses of the sheets 41, 42, 43, and 44 are each set to be 1.0 mm. First, the sheet 42 for the parent bladder 23 and the sheet 43 for the child bladder 24 that is to be adjacent thereto are overlaid in the thickness direction Z, the approximate center of the region at which the sheets 42 and 43 were overlaid is welded (or adhered) in a ring shape (the ring-shaped welded location is denoted by reference numeral 49m), and the inner side of the welded location is cut off to form the through hole 49. Also, an approximately cylindrical nipple 45 is attached to the sheet 44 through welding or adhesion, and the portion of the sheet 44 that corresponds to the inner radius of the nipple 45 penetrates therethrough such that air can flow therethrough (the welded location around the nipple 45 is denoted by reference numeral 45m). Next, the edge portions 41c, 41d, 41e, and 41f of the sheet 41 for the parent bladder 23 are made to oppose the edge portions 42c, 42d, 42e, and 42f of the sheet 42, and the opposing edge portions are welded (or adhered) in a state of being overlaid facing outward (the welded location around the sheets 41 and 42 are denoted by reference numeral 23m in FIG. 7). Also, the edge portions 43c, 43d, 43e, and 43f of the sheet 43 for the child bladder 24 are made to oppose the edge portions 44c, 44d, 44e, and 44f of the sheet 44, and the opposing edge portions are welded (or adhered) in a state of being overlaid facing outward (the welded location around the sheets 43 and 44 are denoted by reference numeral 24m in FIG. 7). Accordingly, the air bladder 22 including a second air bladder region A2 is obtained easily and inexpensively.

Figure 8A:
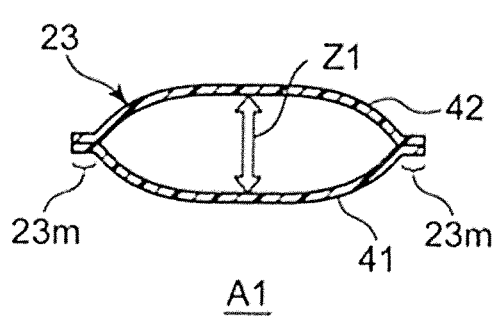
FIGS. 8(A) and 8(B) are diagrams showing cross-sections taken when the air bladder shown in FIG. 7 is cut along a width direction X into different regions (regions A1 and A2 in FIG. 7) in the lengthwise direction in a state in which the air bladder has been supplied with a small amount of air.
Figure 8B:
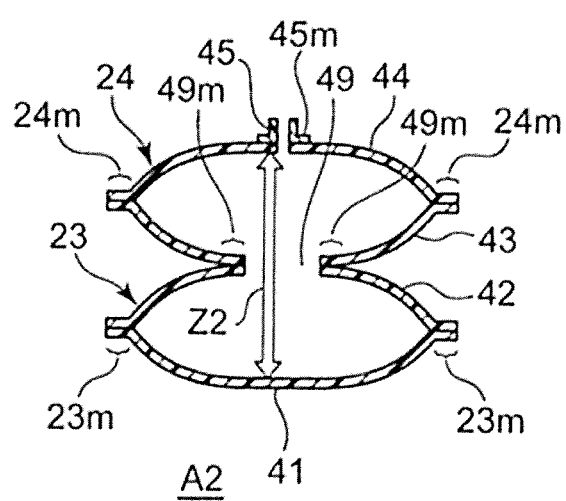

FIGS. 8(A) and 8(B) show cross sections obtained by cutting the air bladder 22 along the width direction X in different regions A1 and A2 in the lengthwise direction Y, in a state in which a small amount of air has been supplied to the air bladder 22 through the nipple 45 from the outside. Since the parent bladder 23 and the child bladder 24 communicate through the through hole 49, the parent bladder 23 and the child bladder 24 are inflated to the same pressure and swell. Here, when the first fluid bladder region A1 and the second fluid bladder region A2 are inflated to a certain pressure (Pc1), the first fluid bladder region A1 swells by a certain stroke amount Z1 in the thickness direction Z. At this time, the stroke amount Z1 of the first fluid bladder region A1 is suppressed to a level corresponding to the parent bladder 23 (one bladder). On the other hand, in the second fluid bladder region A2, the child bladder 24 is overlaid on the parent bladder 23 in the thickness direction Z. Accordingly, when the second fluid bladder region A2 swells in the thickness direction Z, the stroke amount Z2 of the second fluid bladder region A2 increases to a level corresponding to the parent bladder 23 and the child bladder 24 (two bladders). As a result, the second fluid bladder region A2 swells in the thickness direction by the stroke amount Z2, which is larger than the stroke amount Z1 of the first fluid bladder region A1.

Figure 3:
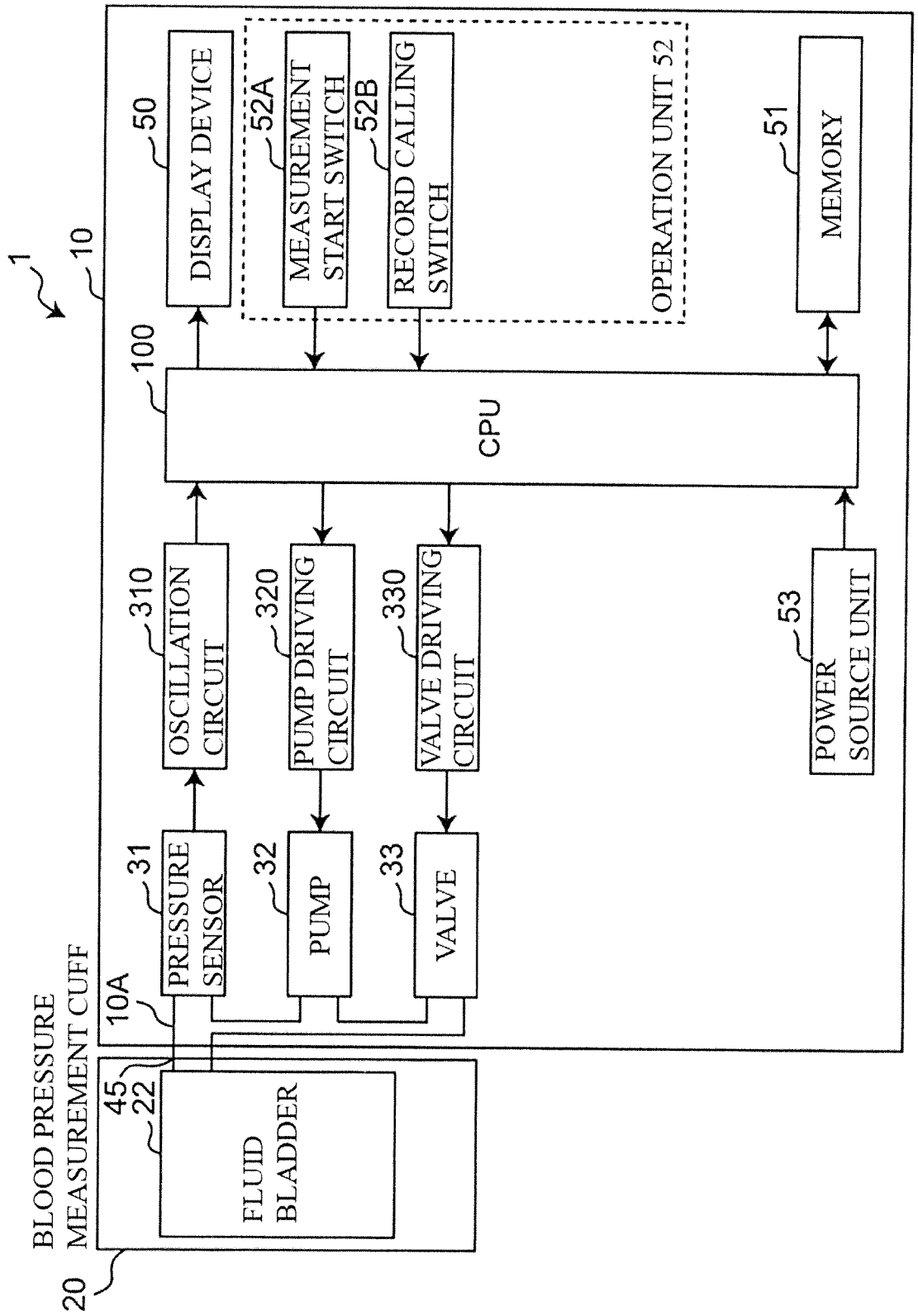
FIG. 3 is a diagram showing a schematic block configuration of the blood pressure monitor.

The air bladder 22 is contained in the cuff 20 in a state in which the nipple 45 attached to the sheet 41 protrudes through the outer cloth 20A. When the main body 10 and the cuff 20 are joined, an air tube 10A of the main body 10 is fit air-tightly into the nipple 45 of the air bladder 22, as shown in FIG. 3. The main body 10 and the cuff 20 are joined together through a joining means (an engaging protrusion and a depression with which the engaging protrusion engages, adhesive, etc.) (not shown). Thus, the main body 10 and the cuff 20 are integrated.

FIG. 3 shows a schematic block configuration of the cuff 20 and the main body 10 of the blood pressure monitor 1. The blood pressure monitor 1 includes a CPU 100 serving as a control unit, a display device 50, a memory 51 serving as a storage unit, an operation unit 52, a power source unit 53, a pump 32, a valve 33, and a pressure sensor 31, which are mounted in the main body 10. Also, the main body 10 includes an oscillation circuit 310 that converts the output from the pressure sensor 31 into a frequency, a pump driving circuit 320 that drives the pump 32, and a valve driving circuit 330 that drives the valve 33, which are mounted in the main body 10.

The display device 50 includes a display, an indicator, and the like, and displays predetermined information such as blood pressure measurement results in accordance with a control signal from the CPU 100.

The operation unit 52 includes a measurement start switch 52A for receiving an instruction to start measuring the blood pressure, and a record calling switch 52B for calling a blood pressure measurement result stored in the memory. The switches 52A and 52B input operation signals corresponding to user instructions to the CPU 100.

The memory 51 stores data of programs for controlling the blood pressure monitor 1, data used to control the blood pressure monitor 1, setting data for setting various functions of the blood pressure monitor 1, data of measurement results of blood pressure values, and the like. Also, the memory 51 is used as a work memory or the like for when a program is executed.

The CPU 100 performs control for driving the pump 32 and the valve 33 according to an operation signal from the operation unit 52, in accordance with a program for controlling the blood pressure monitor 1, which is stored in the memory 51. Also, based on the signal from the pressure sensor 31, the CPU 100 calculates the blood pressure values and controls the display device 50 and the memory 51.

The power source unit 53 supplies power to the CPU 100, the pressure sensor 31, the pump 32, the valve 33, the display device 50, the memory 51, the oscillation circuit 310, the pump driving circuit 320, and the valve driving circuit 330.

The pump 32, the valve 33, and the pressure sensor 31 are connected via a common air tube 10A to the air bladder 22 contained in the cuff 20. The pump 32 supplies air to the air bladder 22 through the air tube 10A in order to increase the pressure (cuff pressure) in the air bladder 22 contained in the cuff 20. The valve 33 is a solenoid valve that is controlled to open and close through energization, and is used to control the cuff pressure by discharging or sealing the air in the air bladder 22 through the air tube 10A. The pump driving circuit 320 drives the pump 32 based on a control signal provided from the CPU 100. The valve driving circuit 330 opens and closes the valve 33 based on a control signal provided from the CPU 100.

In this example, the pressure sensor 31 is a piezoresistant pressure sensor that detects the pressure of the cuff 20 (air bladder 22) through the air tube 10A and outputs the pressure as a cuff pressure signal (denoted by reference numeral Pc) in a time series. The oscillation circuit 310 oscillates based on an electrical signal value obtained based on a change in electrical resistance caused by the piezoresistant effect from the pressure sensor 31, and outputs a frequency signal having a frequency corresponding to the electrical signal value of the pressure sensor 31 to the CPU 100.

Figure 2:
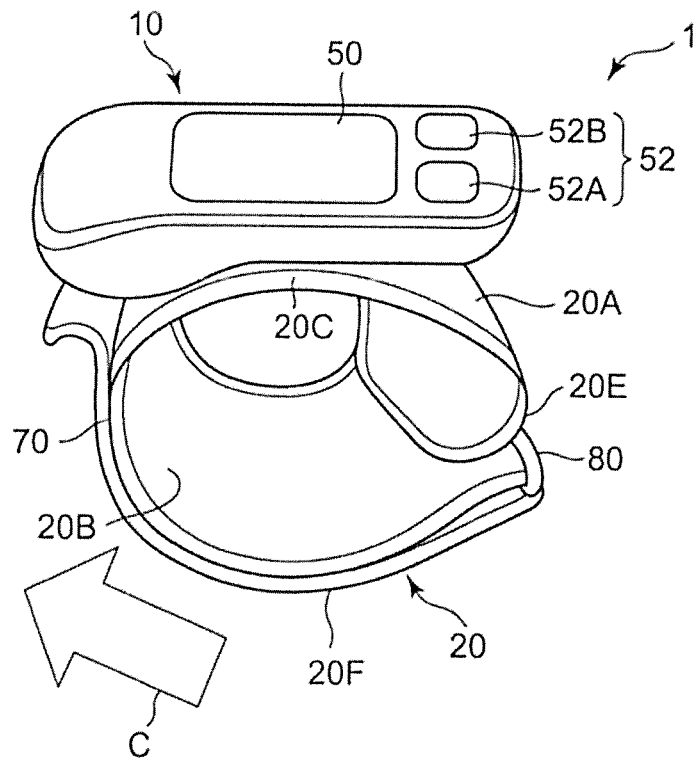
FIG. 2 is a perspective view showing a state of the blood pressure monitor when attached to a measurement site (not shown).

When the blood pressure monitor 1 (cuff 20) is attached to the wrist 90 serving as the measurement site, the wrist 90 is passed through the center of the cuff 20 as indicated by the arrow A in FIG. 1, with the back of the hand facing upward. Accordingly, the second portion 20C of the cuff 20 is mounted on the wrist 90 along with the main body 10. Next, the portion of the third portion 20F of the cuff 20 that is away from the main body 10 is passed through the ring 80, is pulled downward and to the right in FIG. 1 as indicated by the arrow B, and is folded over as indicated by the arrow C in FIG. 2. Then, the folded-over portion is fixed by being pressed onto the planar fastener 70.

Figure 14:
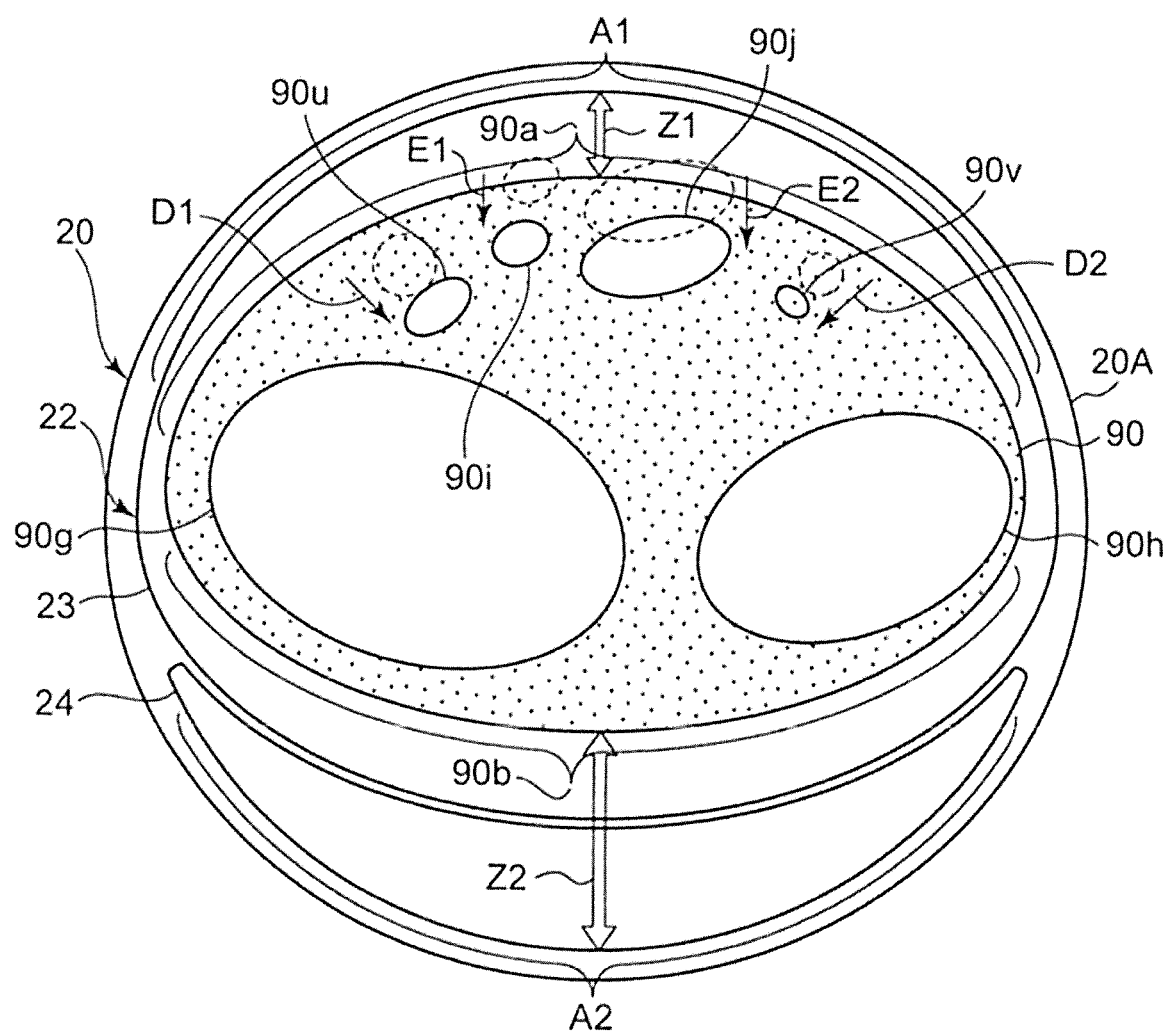
FIG. 14 is a diagram showing a cross section taken orthogonally to a wrist, in a state in which the blood pressure monitor (cuff) shown in FIG. 1 is attached to the wrist.

FIG. 14 shows a cross section taken orthogonally to the wrist 90 with the cuff 20 attached to the wrist 90. With the cuff 20 attached to the wrist 90, the first fluid bladder region A1 of the air bladder 22 corresponds to the half surface (in FIG. 14, the half surface on the upper side) 90a on the palm side. On the other hand, the second fluid bladder region A2 of the air bladder 22 corresponds to the half surface (in FIG. 14, the half surface on the lower side) 90b on the back side. A radius 90g and an ulna 90h are included in the wrist 90. A palmaris longus tendon 90i and a flexor digitorum superficialis tendon 90j pass through the approximate center near the half surface 90a on the palm side. A radial artery 90u passes between the palmaris longus tendon 90i and the radius 90g, and an ulnar artery 90v passes between the flexor digitorum superficialis tendon 90j and the ulna 90h. Note that in FIG. 14, for the sake of simplicity, the inner cloth 20B is not illustrated, and the parent bladder 23 is schematically illustrated as being wrapped continuously around the wrist 90.

Figure 4:
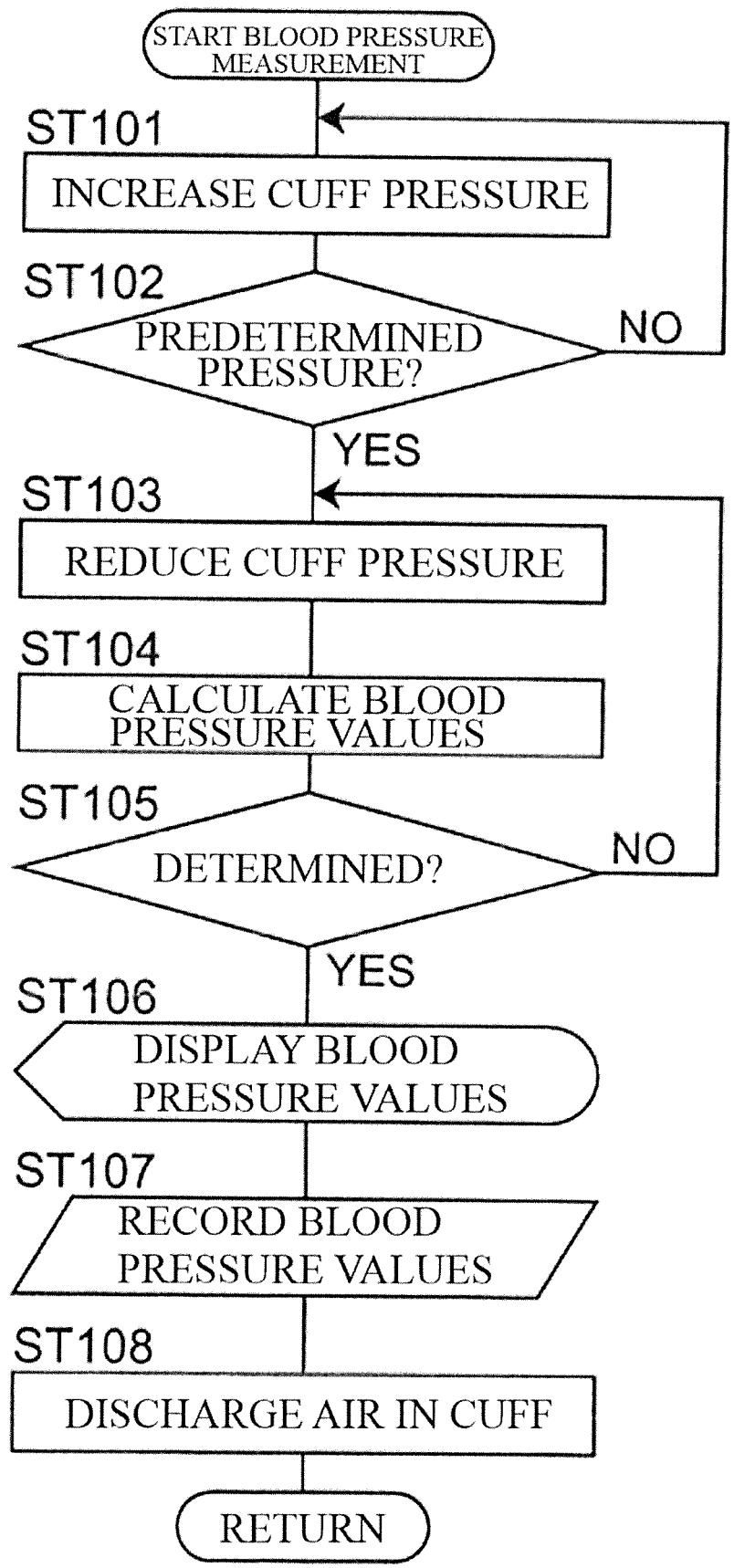
FIG. 4 is a diagram showing a control flow for the blood pressure monitor.

In the blood pressure monitor 1, the blood pressure values of the measurement subject are measured by the CPU 100 through an oscillometric method in accordance with the flow shown in FIG. 4.

Specifically, when the measurement start switch 52A is pressed (turned on), the blood pressure monitor 1 starts blood pressure measurement as shown in FIG. 4. When blood pressure measurement is started, the CPU 100 initializes a memory region for processing and outputs a control signal to the valve driving circuit 330. Based on the control signal, the valve driving circuit 330 opens the valve 33 to discharge the air in the air bladder 22 of the cuff 20. Next, control for adjusting the pressure sensor 31 to 0 mmHg is performed.

When the blood pressure measurement is started, first, the CPU 100 closes the valve 33 via the valve driving circuit 330, and thereafter performs control for driving the pump 32 via the pump driving circuit 320 and sending air to the air bladder 22. Accordingly, the air bladder 22 swells and the cuff pressure gradually increases (step ST101). At this time, the first fluid bladder region A1 and the second fluid bladder region A2 of the air bladder 22 are inflated to the same pressure and swell.

When the cuff pressure is increased and reaches a predetermined pressure (YES in step ST102), the CPU 100 performs control for stopping the pump 32 via the pump driving circuit 320 and thereafter gradually open the valve 33 via the valve driving circuit 330. Accordingly, the air bladder 22 contracts and the cuff pressure gradually decreases (step ST103).

Here, the predetermined pressure is a pressure that is sufficiently higher than the systolic blood pressure of the measurement subject (e.g., systolic blood pressure+30 mmHg), and is stored in advance in the memory 51, or is determined by the CPU 100 estimating the systolic blood pressure using a predetermined calculation equation during increase of the cuff pressure (e.g., see JP 2001-70263A).

Also, regarding the pressure reduction rate, the target pressure reduction rate is set during inflation of the cuff, and the CPU 100 controls the opening degree of the valve 33 so as to achieve the target pressure reduction rate (see JP 2001-70263A).

In the pressure reduction process, the pressure sensor 31 detects the pressure of the cuff 20 and outputs the cuff pressure signal Pc. Based on the cuff pressure signal Pc, the CPU 100 applies a known algorithm using an oscillometric method and calculates the blood pressure values (systolic blood pressure and diastolic blood pressure) (step ST104). Note that the calculation of the blood pressure values is not limited to the pressure reduction process and may be performed in the pressure increase process.

When the blood pressure values are calculated and determined (YES in step ST105), the CPU 100 performs control for displaying the calculated blood pressure values on the display device 50 (step ST106) and storing the blood pressure values in the memory 51 (step ST107).

When the measurement ends, the CPU 100 performs control for opening the valve 33 via the valve driving circuit 330 and discharging the air in the air bladder 22 of the cuff 20 (step ST108).

In the case of performing the blood pressure measurement in this way, in the blood pressure monitor 1, when the first fluid bladder region A1 and the second fluid bladder region A2 are inflated to a certain pressure (the same pressure) Pc1 as shown in FIG. 14, the stroke amount Z2 by which the second fluid bladder region A2 swells is larger in the thickness direction Z than the stroke amount Z1 by which the first fluid bladder region A1 swells. Conversely, the first fluid bladder region A1 merely swells less compared to the case where there is no second fluid bladder region A2, or the case where the stroke amount by which the second fluid bladder region A2 swells is less than or equal to the stroke amount by which the first fluid bladder region A1 swells. Accordingly, the distance (denoted by the arrows D1 and D2) by which the arteries 90$u$ and 90$v$ in the wrist 90 serving as the measurement site withdraw due to being pressed by the first fluid bladder region A1 decreases, and the extra inflation amount for pressing the arteries 90$u$ and 90$v$ decreases. Specifically, rather than the first fluid bladder region swelling toward the soft tissue between the palmaris longus tendon 90$i$ and the radius 90$g$ and between the flexor digitorum superficialis tendon 90$j$ and the ulna 90$h$, a state is entered in which the entirety of the half surface 90$a$ on the palm side including the tendons 90$i$ and 90$j$ is compressed in a dispersed manner as indicated by the arrows E1, E2, D1, and D2. Accordingly, the distances D1 and D2 by which the arteries 90$u$ and 90$v$ withdraw decreases, and the extra pressure amount for pressing the arteries 90$u$ and 90$v$ decreases. As a result, the measured values for blood pressure measured through inflation using the cuff 20 (the first fluid bladder region A1) can be brought closer to the true values and measurement accuracy can be increased.

Also, in this example, during inflation for blood pressure measurement, in order to control the cuff pressure Pc, the CPU 100 mounted in the blood pressure monitor main body 10 need only control the supply of air to the air bladder 22 (includes the first and second air bladder regions A1 and A2) using the pump 32 and the discharge of air from the air bladder 22 using the valve 33. Accordingly, control of the cuff pressure Pc is simplified compared to the case of including an element that expands or swells due to action of a different type than the fluid bladder, such as an actuator, for example, instead of the second fluid bladder region A2 as the expansion region corresponding to the half surface 90$b$ on the back side.

In the example above, there is one child bladder 24 included in the air bladder 22, but there is no limitation to this. Two or more child bladders 24 may be overlaid on the parent bladder 23 in the thickness direction Z. In this case, through holes 49 are formed in sheets that are mutually adjacent to the multiple child bladders, and the air serving as the fluid can flow from the child bladder 24 on the uppermost level, to which the nipple is attached, to the parent bladder 23 on the lowermost level. In this case, when the second fluid bladder region A2 swells in the thickness direction Z, the stroke amount of the second fluid bladder region A2 increases to a level corresponding to the parent bladder 23 and the two or more child bladders 24. As a result, the second fluid bladder region A2 swells in the thickness direction Z by an even larger stroke amount. As a result, the measured values for blood pressure measured through inflation using the cuff 20 can be brought even closer to the true values and measurement accuracy can be further increased.

Second Embodiment

Figure 10A:
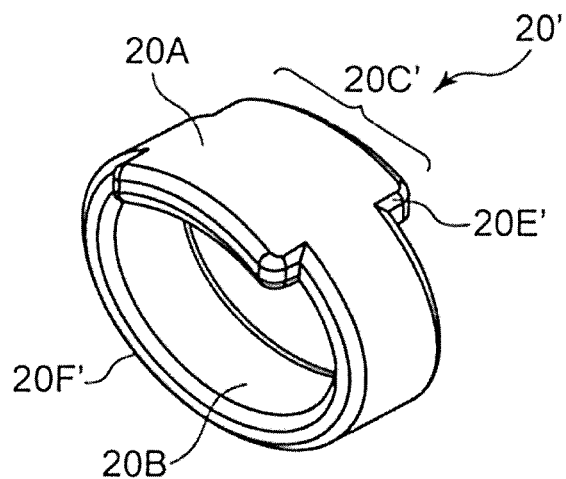
FIG. 10(A) is a diagram schematically showing a perspective view of the exterior of a blood pressure measurement cuff according to another embodiment of the present invention.
Figure 10B:
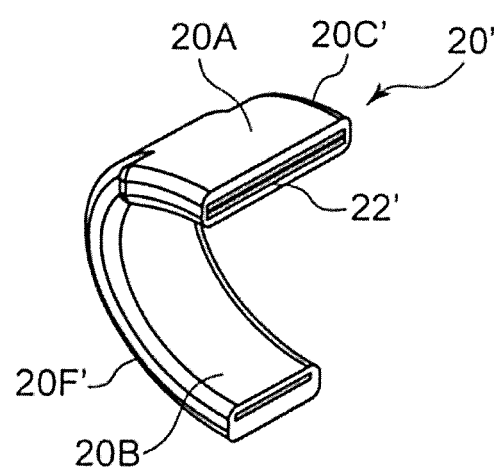
FIG. 10(B) is a diagram showing a state in which the cuff shown in FIG. 10(A) has been cut by a vertical plane. Also.
Figure 10C:
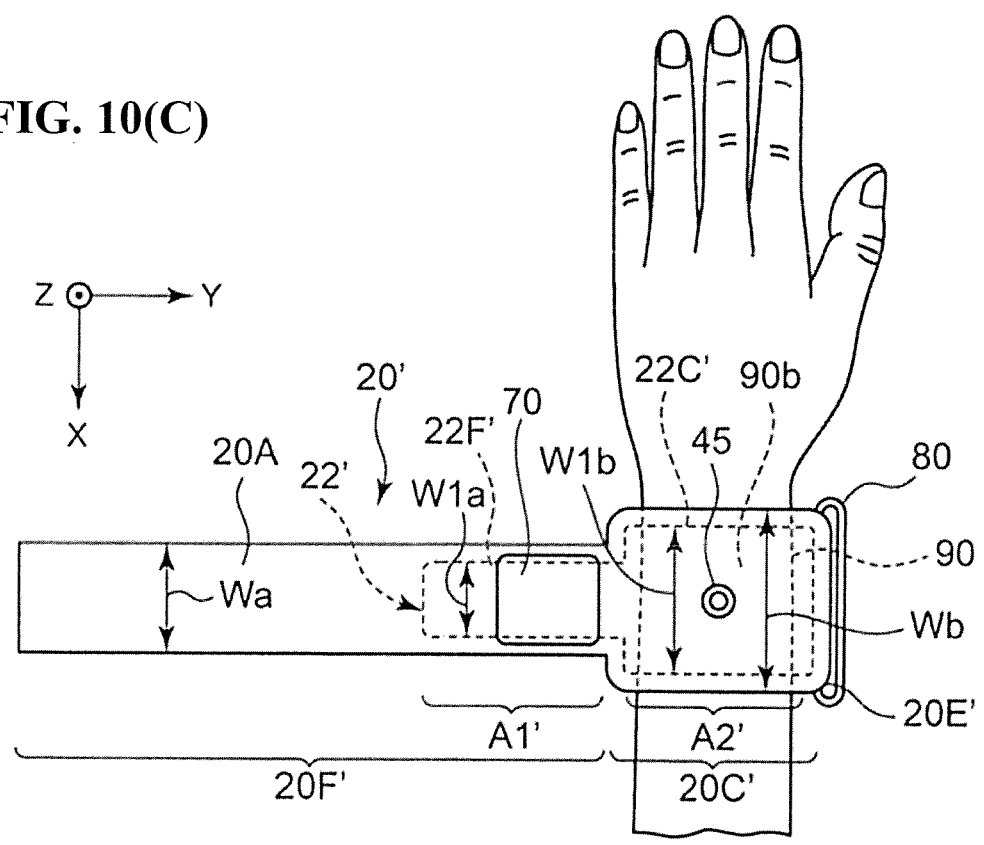
FIG. 10(C) is a diagram schematically showing a planar layout in a view of a surface corresponding to the outer circumferential side in FIG. 10(A) in a state in which the cuff is unfolded.

FIG. 10(A) schematically shows a perspective view of the exterior of a blood pressure measurement cuff 20' according to another embodiment of the present invention. Also, FIG. 10(B) shows a state in which the cuff 20' shown in FIG. 10(A) has been cut by a vertical plane. Also, FIG. 10(C) schematically shows a plane layout for when viewing a surface corresponding to the outer circumferential side in FIG. 10(A) with the cuff 20' unrolled. Note that in FIGS. 10(A) and 10(B), for the sake of simplicity, the nipple 45, the planar fastener 70, and the ring 80 for folding over are not illustrated, and the cuff 20' is illustrated schematically as a continuous ring shape (the same follows for FIGS. 11(A) and 11(B), which will be described later). Constituent elements that are the same as the constituent elements in FIGS. 5 and 6 are denoted by the same reference numerals, and detailed description thereof is omitted as appropriate.

As shown in FIGS. 10(A), 10(B), and 10(C), the cuff 20' is formed as a bladder-shaped band member by sewing the outer cloth 20A and the inner cloth 20B along their circumferential edges.

In this example, as can be understood from FIG. 10(C), along the lengthwise direction Y of the cuff 20', the cuff 20' includes an approximately rectangular wide portion 20C' that corresponds to the half surface 90b on the back side, and a band-shaped narrow portion 20F' that is continuous with the wide portion 20C' and extends to the left side in FIG. 10(C). For example, the dimension in the lengthwise direction Y of the wide portion 20C' is set to fall within the range of about 50 mm to 100 mm, and the dimension in the lengthwise direction Y of the narrow portion 20F' is set to fall within the range of about 200 mm to 300 mm. Also, the dimension Wa of the width direction X of the narrow portion 20F' is set to fall within a range in which Wa=30 mm to 60 mm. The dimension Wb in the width direction X of the wide portion 20C' is set to be about 10 mm larger than the width direction dimension Wa of the narrow portion 20F'.

A ring 80 having a substantially oval shape is attached to the right end 20E' in FIG. 10(C) of the wide portion 10C'. Also, the planar fastener 70 is attached to the surface of the portion of the narrow portion 20F' of the cuff 20' that is closest to the wide portion 20C'.

An air bladder 22' serving as a fluid bladder for compressing the wrist 90 is contained in the cuff 20' spanning from the wide portion 20C' to the narrow portion 20F'.

The air bladder 22' includes an approximately rectangular wide portion 22C' that is contained in the wide portion 20C' of the cuff 20', and a band-shaped narrow portion 22F' that is continuous with the wide portion 22C' and extends to the left side in FIG. 10(C).

In this example, the dimension in the lengthwise direction Y of the wide portion 22C' is set to be about 5 mm to 10 mm smaller than the dimension in the lengthwise direction Y of the wide portion 20C' of the cuff 20'. The dimension in the lengthwise direction Y obtained by adding the wide portion 22C' and the narrow portion 22F' is set to be about half of the dimension in the lengthwise dimension Y of the cuff 20'. Also, the dimension W1a in the width direction X of the narrow portion 22F' and the dimension W1b in the width direction X of the wide portion 22C' are each set to be about 5 mm smaller than the width direction dimension Wa of the narrow portion 20F' and the width direction dimension Wb of the wide portion 20C' of the cuff 20' respectively.

Here, the portion (included in the narrow portion 20F') of the air bladder 22' extending in the lengthwise direction Y, the portion corresponding to the half surface 90a on the palm side, is referred to as the first fluid bladder region A1'. On the other hand, the portion (approximately corresponds to the wide portion 20C') of the air bladder 22' that corresponds to the half surface 90b on the back side is referred to as the second fluid bladder region A2'.

In the case of producing the air bladder 22', an approximately flat sheet to which a nipple 45 is attached through welding (or adhesion) and another approximately flat sheet are made to oppose each other in the thickness direction Z, and are welded (or adhered) with the opposing edge portions overlapped facing outward through a known means, along the outline indicated by the broken line in FIG. 10(C). Accordingly, the air bladder 22' including a second air bladder region A2' is obtained easily and inexpensively. The material of the sheets forming the air bladder 22' is polyurethane resin in this example. For example, the thicknesses of the sheets are each set to 1.0 mm.

The cross section (cross section obtained by cutting along the width direction X) of the obtained air bladder 22' is about the same as the cross section shown in FIG. 8(A).

The air bladder 22' is contained in the cuff 20' with the nipple 45 protruding through the outer cloth 20A. When the cuff 20' is joined to the blood pressure monitor main body 10, in this example, the nipple 45 and the air tube 10A (see FIG. 3) of the main body 10 are connected by a flexible elongated air tube 10B (see FIG. 16). Accordingly, the blood pressure monitor (denoted by reference numeral 1') including the cuff 20' and the main body 10 is formed.

When the cuff 20' is attached to the wrist 90 serving as the measurement site, the wrist 90 is passed through the center of the cuff 20' similarly to the manner indicated by the arrow A in FIG. 1, with the back of the hand facing upward. Accordingly, the wide portion 20C' of the cuff 20' is mounted on the wrist 90. Next, the portion of the narrow portion 22F' of the cuff 20' that is away from the main body 10 is passed through the ring 80, is pulled downward and to the right in FIG. 1 as indicated by the arrow B, and is folded over as indicated by the arrow C in FIG. 2. Then, the folded-over portion is fixed by being pressed onto the planar fastener 70.

Figure 15:
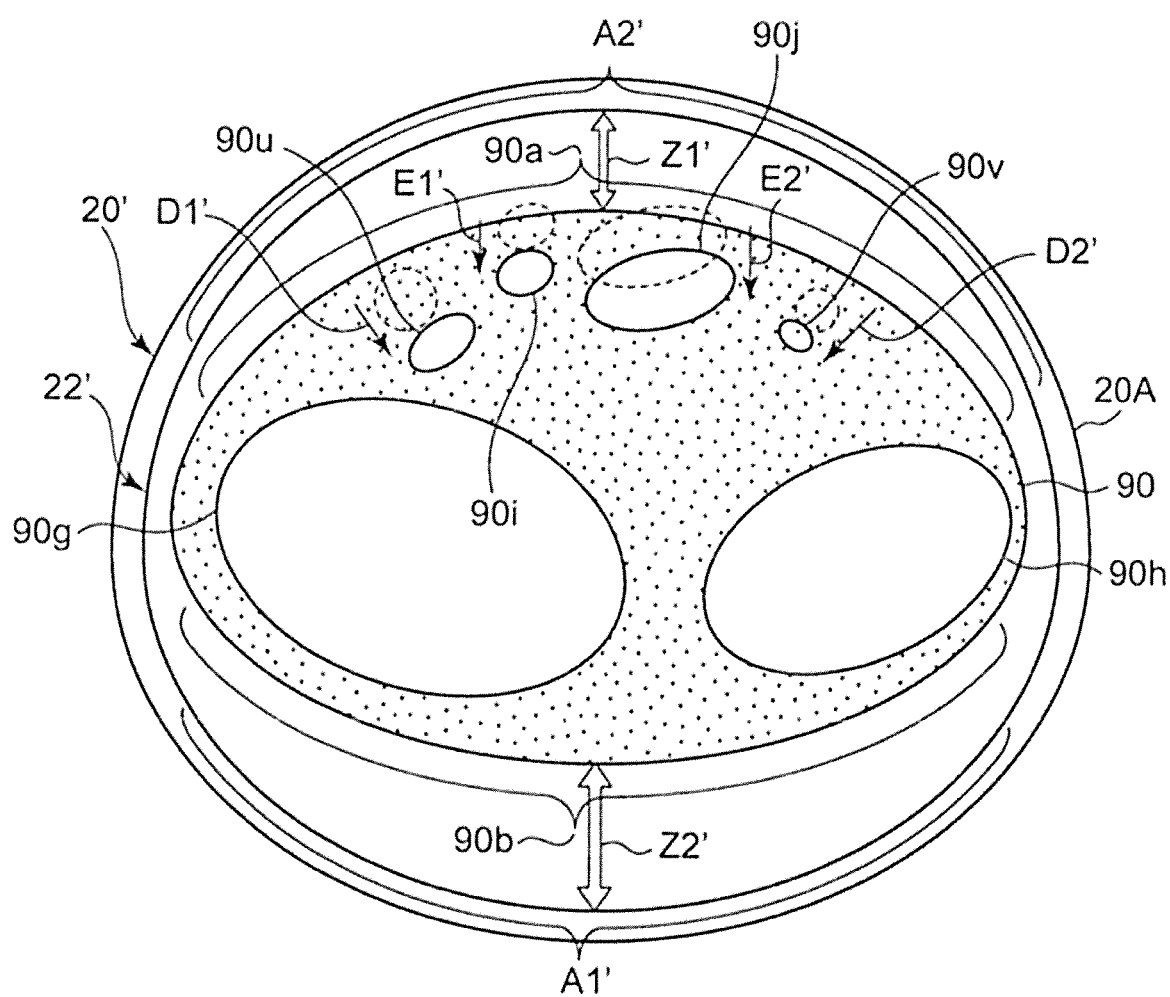
FIG. 15 is a diagram showing a cross section taken orthogonally to the wrist, in a state in which the cuff shown in FIG. 10(A) is attached to the wrist.

FIG. 15 shows a cross section taken orthogonally to the wrist 90 with the cuff 20' attached to the wrist 90. With the cuff 20' attached to the wrist 90, the first fluid bladder region A1' of the air bladder 22' corresponds to the half surface (in FIG. 15, the half surface on the upper side) 90a on the palm side. On the other hand, the second fluid bladder region A2' of the air bladder 22' corresponds to the half surface (the half surface on the lower side in FIG. 15) 90b on the back side. Note that in FIG. 15, for the sake of simplicity, the inner cloth 20B is not illustrated, and the air bladder 22' is schematically illustrated as being wrapped continuously around the wrist 90.

In the blood pressure monitor 1', the blood pressure values of the measurement subject are measured through an oscillometric method in accordance with the flow shown in FIG. 4, similarly to the description of the first embodiment.

In the case of performing blood pressure measurement in this way, in the blood pressure monitor 1', when the first fluid bladder region A1' and the second fluid bladder region A2' are inflated to the certain pressure (the same pressure) Pc1 as shown in FIG. 15, the stroke amount Z2' by which the second fluid bladder region A2' swells is larger in the thickness direction Z than the stroke amount Z1' by which the first fluid bladder region A1' swells. The reason for this is because if the cross-sections of the fluid bladder regions approach a circular shape as they swell and the width direction dimension of the fluid bladder region increases, the stroke amount in the thickness direction Z of the fluid bladder region also increases accordingly. Conversely, the first fluid bladder region A1' merely swells less compared to the case where there is no second fluid bladder region A2', or the case where the stroke amount by which the second fluid bladder region A2' swells is less than or equal to the stroke amount by which the first fluid bladder region A1' swells. Accordingly, the distance (denoted by the arrows D1' and D2') by which the arteries 90u and 90v in the wrist 90 serving as the measurement site withdraw due to being pressed by the first fluid bladder region A1' decreases, and the extra inflation amount for pressing the arteries 90u and 90v decreases. Specifically, rather than the first fluid bladder region A1' swelling toward the soft tissue between the palmaris longus tendon 90i and the radius 90g and between the flexor digitorum superficialis tendon 90j and the ulna 90h, a state is entered in which the entirety of the half surface 90a on the palm side including the tendons 90i and 90j is compressed in a dispersed manner as indicated by the arrows E1', E2', D1', and D2'. Accordingly, the distances D1' and D2' by which the arteries 90u and 90v withdraw decrease, and the extra pressure amount for pressing the arteries 90u and 90v decreases. As a result, the measured values for blood pressure measured through inflation using the cuff 20' can be brought closer to the true values and measurement accuracy can be increased.

Also, in this example, similarly to the description of the first embodiment, the CPU 100 mounted in the blood pressure monitor main body 10 need only control the supply of air to the air bladder 22' (includes the first and second fluid bladder regions A1' and A2') using the pump 32 and the discharge of air from the air bladder 22' using the valve 33 in order to control the cuff pressure Pc during inflation for blood pressure measurement. Accordingly, control of the cuff pressure Pc is simplified compared to the case of including an element that expands or swells due to action of a different type than the fluid bladder, such as an actuator, for example, instead of the second fluid bladder region A2' as the expansion region corresponding to the half surface 90b on the back side.

Note that the configuration of the second embodiment may be combined with the configuration of the first embodiment. That is, in the cuff 20 of FIGS. 5 and 6, the width direction dimension of the second portion 20C is set to be larger than the width direction dimension of the first portion 20E and the third portion 20F, and the width direction dimension of the second fluid bladder region A2 of the air bladder 22 is set to be larger than the width direction dimension of the first fluid bladder region A1 accordingly. Accordingly, in the state shown in FIG. 14, the stroke amount Z2 by which the second fluid bladder region A2 swells can be made larger in the thickness direction Z than the stroke amount Z1 by which the first fluid bladder region A1 swells. Accordingly, the measurement accuracy can be further increased.

Modified Example 1

In the examples shown in FIGS. 10(A) to 10(C) above, the cuff 20' included an approximately rectangular wide region 20C' and a band-shaped narrow portion 20F' with a dimension in the width direction X that is smaller than that of the wide portion 20C', but there is no limitation to this. For example, as shown in FIGS. 11(A) to 11(C), the dimension W in the width direction X of the cuff (indicated by reference numeral 20") may change continuously in the lengthwise direction Y.

Figure 11A:
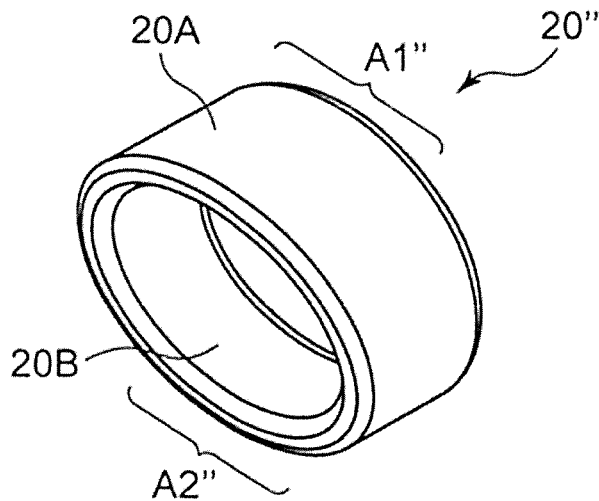
FIG. 11(A) is a diagram schematically showing a perspective view of the exterior of a cuff according to a modified example in which the blood pressure measurement cuff shown in FIG. 10(A).
Figure 11B:
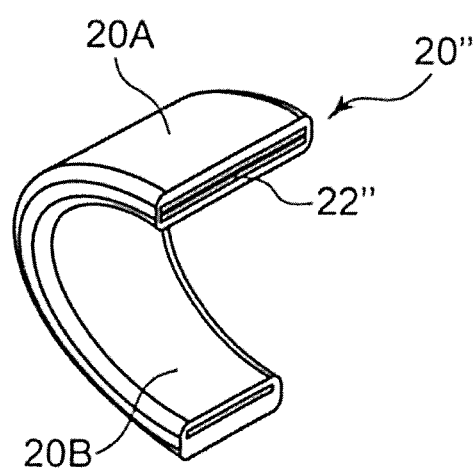
FIG. 11(B) is a diagram showing a state in which the cuff shown in FIG. 11(A) has been cut by a vertical plane. Also.

FIG. 11(A) schematically shows a perspective view of the exterior of this kind of blood pressure measurement cuff 20". Also, FIG. 11(B) shows a state in which the cuff 20" shown in FIG. 11(A) has been cut by a vertical plane. Also, FIG. 11(C)_schematically shows a plane layout for when viewing a surface corresponding to the outer circumferential side in FIG. 11(A) with the cuff 20" unrolled. Constituent elements that are the same as the constituent elements in FIGS. 10(A) to 10(C) are denoted by the same reference numerals, and detailed description thereof is omitted.

Figure 11C:
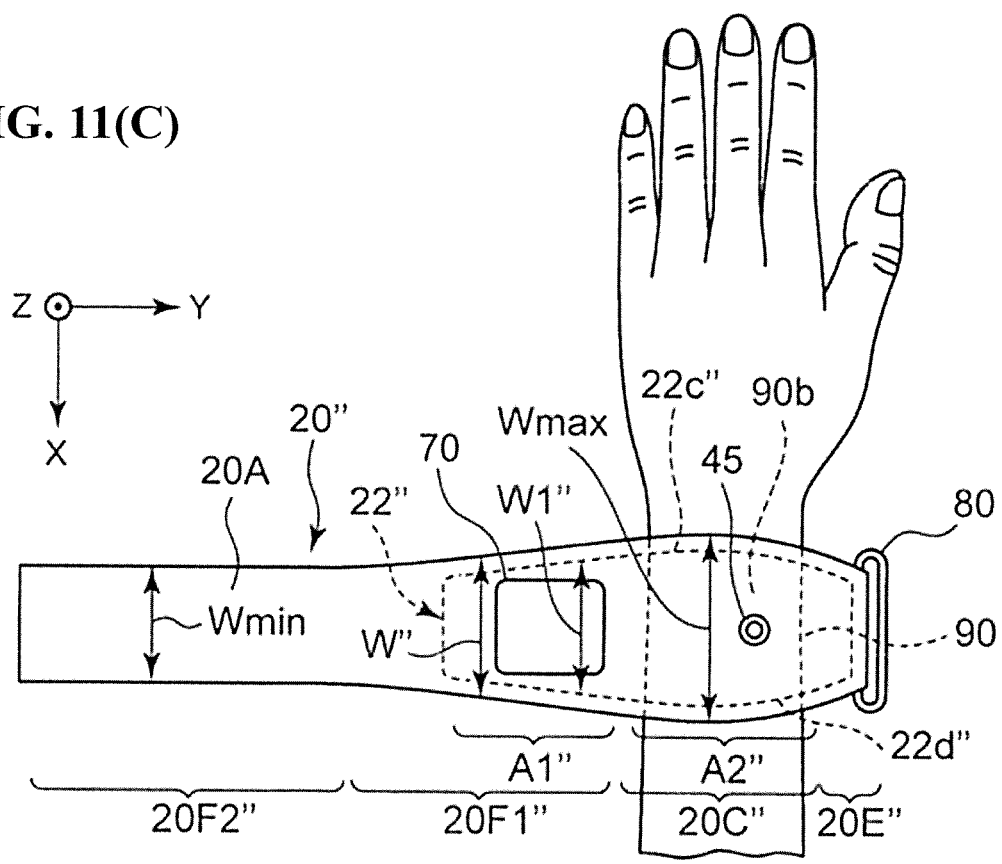
FIG. 11(C) is a diagram schematically showing a planar layout in a view of a surface corresponding to the outer circumferential side in FIG. 11(A) in a state in which the cuff is unfolded.

In this example, as can be understood from FIG. 11(C), along the lengthwise direction Y of the cuff 20", the width direction dimension W" of the cuff 20" has a maximum value Wmax at a portion 20C" corresponding to the half surface 90b on the back side of the wrist 90, the width direction dimension W" gradually decreases at a transition portion 20F1" that extends from the portion 20C" to the left side in FIG. 11(C), and the width direction dimension W" has a minimum value Wmin at a portion 20F2" near the left end in FIG. 11(C). In contrast to this, the width direction dimension W gradually decreases at the portion 20E" near the right end that extends from the portion 20C" corresponding to the half surface 90b on the back side to the right side in FIG. 11(C).

An air bladder 22" serving as a fluid bladder for compressing the wrist 90 is included in the cuff 20", spanning from the portion 20E" near the right end to the transition portion 20F1".

The outlines of the edge portions 22c" and 22d" on both sides in the width direction X of the air bladder 22" are formed to be approximately the same as the outlines of the corresponding edge portions of the cuff 20". The dimension W1" in the width direction X of the air bladder 22" is set to be about 5 mm smaller than the width direction dimension W" of the cuff 20".

Similarly to the air bladder 22' in FIGS. 10(A) to 10(C), in the lengthwise direction Y, the air bladder 22" includes a first fluid bladder region A1" corresponding to the half surface 90a on the palm side of the wrist 90, and a second fluid bladder region A2" corresponding to the half surface 90b on the back side.

The air bladder 22" is produced using the same procedure as the air bladder 22' in FIGS. 10(A) to 10(C) and is contained in the cuff 20" with the same procedure. The material of the sheets forming the air bladder 22" is polyurethane resin in this example.

Also, the cuff 20" is joined to the blood pressure monitor main body 10 using the same procedure as the cuff 20' in FIGS. 10(A) to 10(C). Accordingly, the blood pressure monitor including the cuff 20" and the main body 10 is formed.

According to the blood pressure monitor including the cuff 20", when the first fluid bladder region A1" and the second fluid bladder region A2" are inflated to a certain pressure (the same pressure) Pc1, similarly to the description of FIG. 15, the stroke amount by which the second fluid bladder region A2" swells is larger in the thickness direction Z than the stroke amount by which the first fluid bladder region A1" swells. As a result, the measured values for blood pressure measured through inflation using the cuff 20" can be brought closer to the true values and measurement accuracy can be increased.

Also, in this example, similarly to the description of the first embodiment, the CPU 100 mounted in the blood pressure monitor main body 10 need only control the supply of air to the air bladder 22" (includes the first and second fluid bladder regions A1" and A2") using the pump 32 and the discharge of air from the air bladder 22" using the valve 33 in order to control the cuff pressure Pc during inflation for blood pressure measurement. Accordingly, control of the cuff pressure Pc is simplified compared to the case of including an element that expands or swells due to action of a different type than the fluid bladder, such as an actuator, for example, instead of the second fluid bladder region A2" as the expansion region corresponding to the half surface 90b on the back side.

Modified Example 2

In the examples shown in FIGS. 10(A) to 10(C) above, the air bladder 22' contained in the cuff 20' was obtained by causing an approximately flat sheet to which a nipple 45 is attached through welding (or adhesion) and another approximately flat sheet to oppose each other in the thickness direction, and welding (or adhering) the opposing edge portions in a state of being overlaid facing outward (in the same orientation). However, there is no limitation to this.

Figure 12:
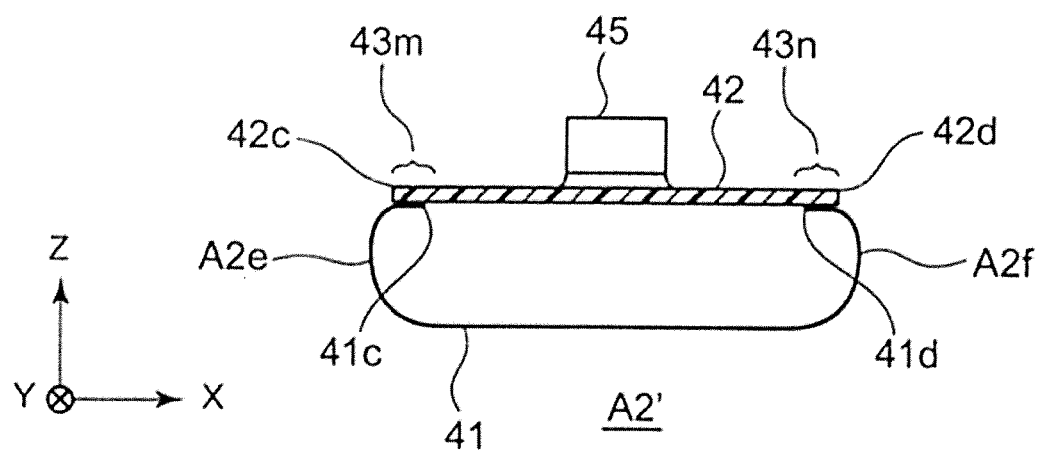
FIG. 12 is a diagram schematically showing a cross section taken when a cuff according to another modified example, which is obtained by modifying the blood pressure measurement cuff shown in FIG. 10(A), is cut along a width direction X.

For example, it is possible to use a structure with a cross section (cross section obtained by cutting along the width direction X) shown in FIG. 12 in the wide portion 22C' (approximately corresponds to the second fluid bladder region A2') of the air bladder 22'. In this example, the approximately flat sheet 42 to which the nipple 45 is attached through welding (or adhesion) and the other sheet 41 with a larger width dimension X than the sheet 42 oppose each other in the thickness direction Z. The sheets 41 and 42 are each composed of polyurethane resin with a uniform thickness, and for example, the thickness of the sheet 41 is set to 0.1 mm and the thickness of the sheet 42 is set to 1.0 mm. In this example, the central portion in the width direction X of the sheet 41 is approximately flat, but the two side portions (which correspond to the side portions A2e and A2f of the second fluid bladder region A2') are curved in an approximately semi-circular shape in cross section toward the sheet 42, and the edge portions 41c and 42c of the sheets 41 and 42 and the edge portions 41d and 42d are welded (or adhered) in a state of being overlaid in mutually opposite orientations (the welded locations on both sides in the width direction X of the sheets 41 and 42 are denoted by reference numerals 43m and 43n in FIG. 12). Note that in this example, the edge portions 41c and 41d of the sheet 41 face inward, and the edge portions 42c and 42d of the sheet 42 face outward.

With the structure of the cross section shown in FIG. 12, when the second fluid bladder region A2' swells in the thickness direction Z, the edge portions of the pair of sheets 41 and 42 do not need to bend in order to open and are not restricted by the inflexibility (stiffness) of the sheet material, unlike the case where the edge portions are overlaid facing outward. As a result, the stroke amount of the second fluid bladder region A2' in the thickness direction Z is even larger. Accordingly, the measurement accuracy can be further increased.

Also, in this example, the thickness (in this example, 0.1 mm) of the side portions A2e and A2f of the second fluid bladder region A2' is thinner than the thickness (in this example, 1.0 mm) of the sheet 42 serving as the sheet portion on the side away from the wrist 90. Accordingly, when the second fluid bladder region A2' swells in the thickness direction Z, it is easier for the side portions A2e and A2f of the second fluid bladder region A2' to stretch. As a result, the stroke amount of the second fluid bladder region A2' in the thickness direction Z is even larger. Accordingly, the measurement accuracy can be further increased.

Also, in addition to this (or instead of this), the hardness of the side portions A2e and A2f of the second fluid bladder region A2' may be made smaller than the hardness of the sheet 42 serving as the sheet portion away from the wrist 90. For example, silicone resin (or polyurethane resin) with a hardness of 50 is used as the material of the sheet 41, and polyurethane resin with a hardness of 80 is used as the material of the sheet 42. In this case, when the second fluid bladder region A2' swells in the thickness direction Z, it is even easier for the side portions A2e and A2f of the second fluid bladder region A2' to stretch. As a result, the stroke amount of the second fluid bladder region A2' in the thickness direction Z is even larger. Accordingly, the measurement accuracy can be further increased.

Modified Example 3

In the example shown in FIG. 12 above, both side portions in the width direction X of the approximately flat sheet 41 are bent toward the sheet 42 to have an approximately semicircular shape in cross section. However, there is no limitation to this.

Figure 13:
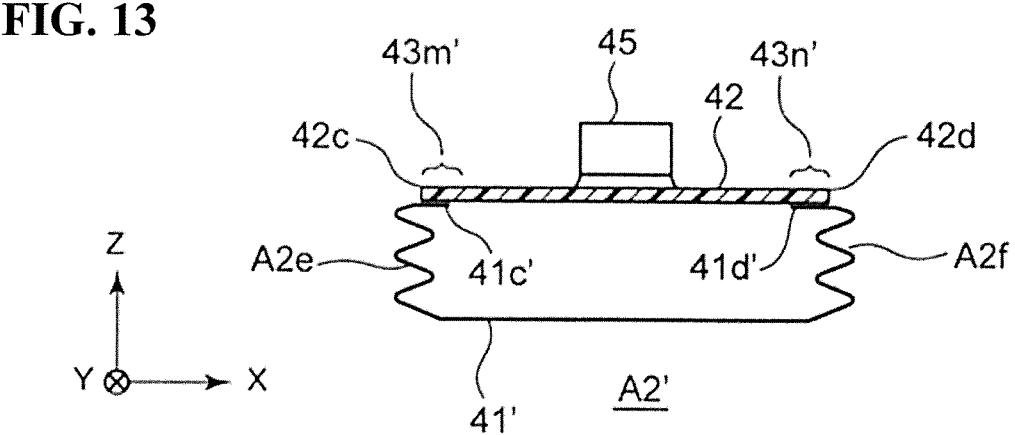
FIG. 13 is a diagram schematically showing a cross section taken when a cuff according to yet another modified example, which is obtained by modifying the blood pressure measurement cuff shown in FIG. 10(A), is cut along the width direction X.

For example, it is possible to use a structure with a cross section (cross section obtained by cutting along the width direction X) shown in FIG. 13 in the wide portion 22C' (approximately corresponds to the second fluid bladder region A2') of the air bladder 22'. In this example, the approximately flat sheet 42 to which the nipple 45 is attached through welding (or adhesion) and the other sheet 41' with a larger width dimension X than the sheet 42 oppose each other in the thickness direction Z. Although the central portion is approximately flat in the width direction X of the sheet 41', both side portions (which correspond to the side portions A2e and A2f of the second fluid bladder region A2') are bellows-shaped in a cross-sectional view along the lengthwise direction Y in their natural state. The sheets 41' and 42 are each composed of polyurethane resin with a uniform thickness, and for example, the thickness of the sheet 41' is set to 0.1 mm and the thickness of the sheet 42 is set to 1.0 mm. The edge portions 41c' and 42c of the sheets 41' and 42 and the edge portions 41d' and 42d are welded (or adhered) in a state of being overlaid in mutually opposite directions (the welded locations on both sides in the width direction X of the sheets 41' and 42 are denoted by reference numerals 43m' and 43n' in FIG. 13).

With the structure of the cross section shown in FIG. 13, when the second fluid bladder region A2' swells in the thickness direction Z, the edge portions of the pair of sheets 41' and 42 do not need to bend in order to open and are not restricted by the inflexibility (stiffness) of the sheet material, unlike the case where the edge portions are overlaid facing outward. As a result, the stroke amount of the second fluid bladder region A2' in the thickness direction Z is even larger. Accordingly, the measurement accuracy can be further increased.

Also, in this example, the thickness (in this example, 0.1 mm) of the side portions A2e' and A2f' of the second fluid bladder region A2' is thinner than the thickness (in this example, 1.0 mm) of the sheet 42 serving as the sheet portion on the side away from the wrist 90. Accordingly, when the second fluid bladder region A2' swells in the thickness direction Z, it is easier for the side portions A2e' and A2f' of the second fluid bladder region A2' to stretch. Furthermore, in this example, the side portions A2e' and A2f' of the second fluid bladder region A2' are bellows-shaped in their natural state. Accordingly, when the second fluid bladder region A2' swells in the thickness direction Z, the bellows-shaped side portions A2e' and A2f' stretch easily. As a result, the stroke amount of the second fluid bladder region A2' in the thickness direction Z is even larger. Accordingly, the measurement accuracy can be further increased.

Note that in this example, the side portions A2e' and A2f' of the second fluid bladder region A2' are bellows-shaped in their natural state, but they may be folded in a zig-zag shape. In this case as well, a similar effect can be exhibited.

The above-described Modified Example 2 and Modified Example 3 can be applied not only to the example shown in FIGS. 10(A) to 10(C), but also to the child bladder 24 shown in FIG. 7, for example.

Also, in the above-described examples, the material of the sheets forming the air bladders 22, 22', and 22" is polyurethane resin, but there is no limitation thereto. The material of the air bladder 22 need only be elastic (in particular, be stretchable and bendable) and be a sturdy material, and for example, silicone resin may be used thereas.

Verification Test

The inventor of the present invention performed a test for verifying the result of the invention by using a commercially-available wrist-type blood pressure monitor (HEM-6310F manufactured by Omron Healthcare Corporation) (indicated by reference numeral 6310) as a standard, on a blood pressure monitor including a cuff of a first comparative example (indicated by reference numeral 820), a blood pressure monitor including the cuff of a second comparative example (indicated by reference numeral 920), and the blood pressure monitor 1 including the cuff 20 of the first embodiment.

Figure 16:
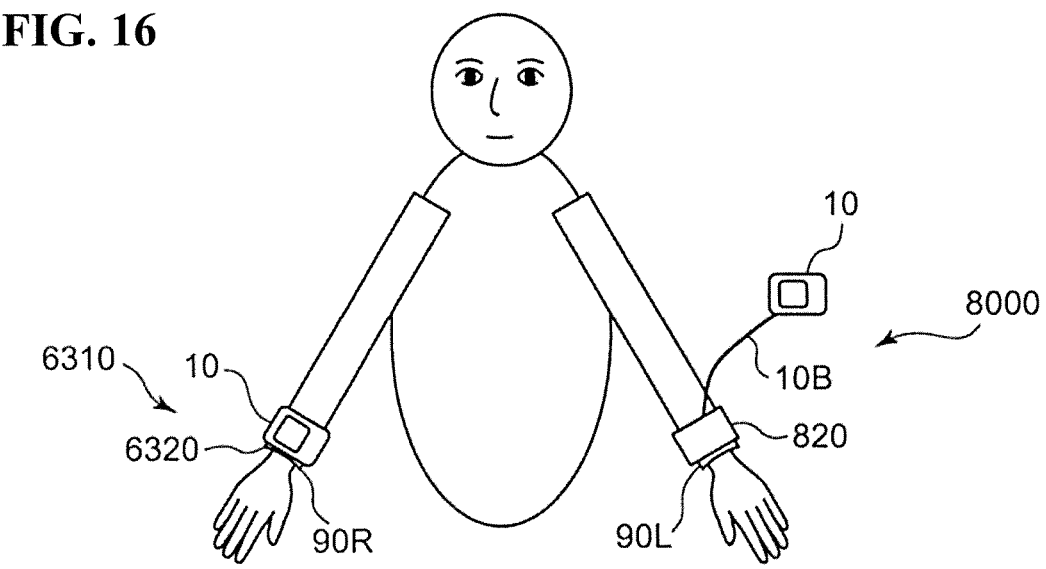
FIG. 16 is a diagram showing a state in which a verification test has been performed regarding the effect of one or more embodiments of the present invention.
Figure 18:
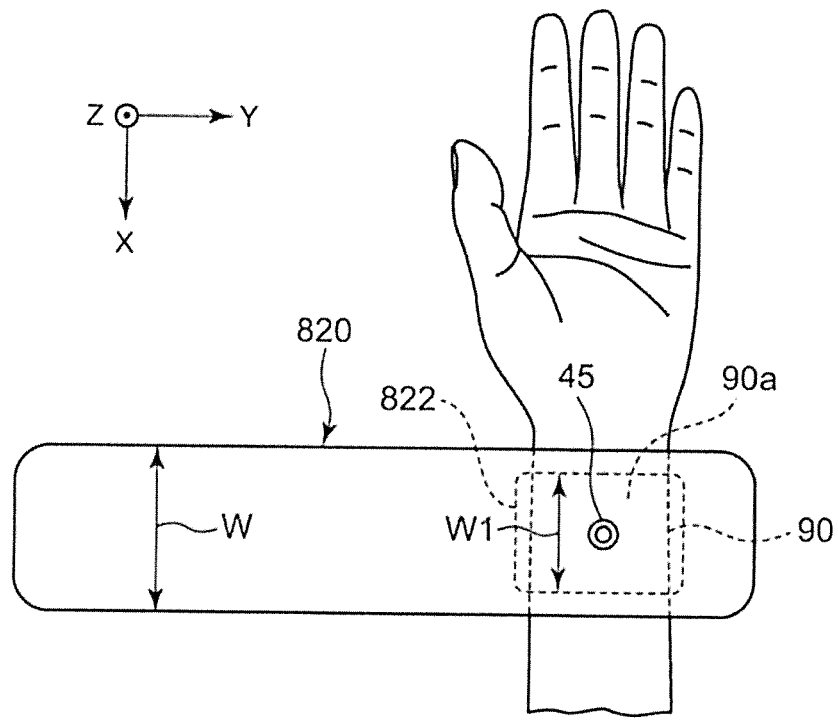
FIG. 18 is a diagram showing a configuration of a cuff according to a first comparative example used in the above-mentioned verification test.

As shown in FIG. 18, the cuff 820 of the first comparative example contains an air bladder 822 having a dimension that approximately corresponds to the half surface 90a on the palm side of the wrist 90 in the lengthwise direction Y. The air bladder 822 is formed by causing a pair of sheets to oppose each other in the thickness direction Z and welding the edge portions of the sheets in a state of being overlaid facing outward. The dimension W in the width direction X of the cuff 820 is set to about 30 mm, and the dimension W1 in the width direction X of the air bladder 822 is set to be about 5 mm smaller than that. As shown in FIG. 16, the cuff 820 is connected to the blood pressure monitor main body 10 via a flexible elongated air tube 10B, whereby the blood pressure monitor (indicated by reference numeral 8000) is formed.

Figure 19:
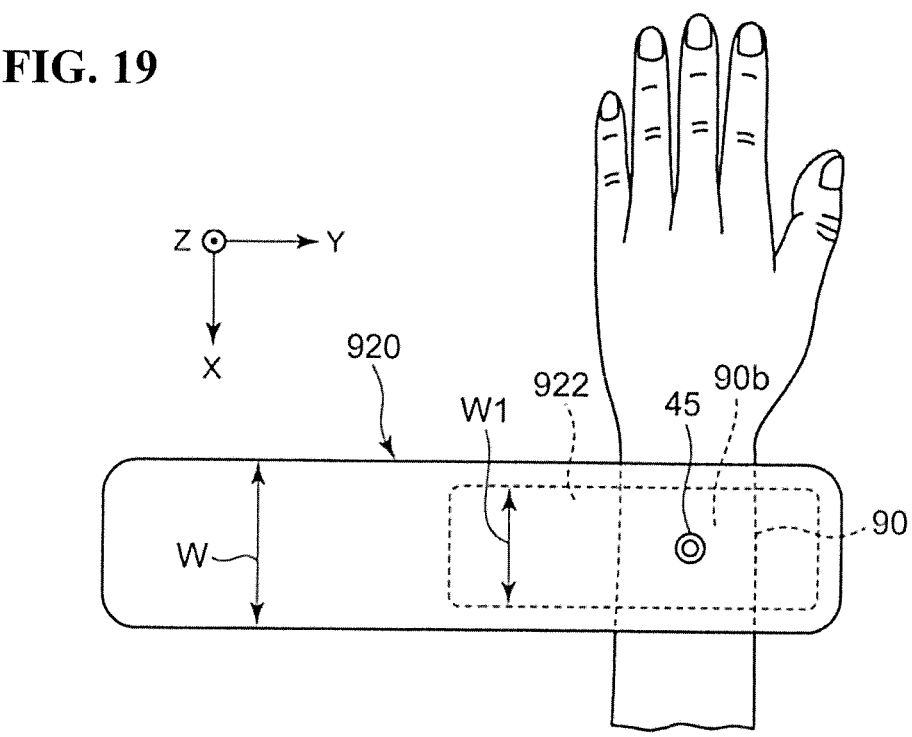
FIG. 19 is a diagram showing a configuration of a cuff according to a second comparative example used in the above-mentioned verification test.

As shown in FIG. 19, the cuff 920 of the second comparative example contains an air bladder 922 having a dimension that approximately corresponds to the half surface 90a on the palm side of the wrist 90 and the half surface 90b on the back side in the lengthwise direction Y. The air bladder 922 is formed by causing a pair of sheets to oppose each other in the thickness direction Z and welding the edge portions of the sheets in a state of being overlaid facing outward. The dimension W in the width direction X of the cuff 920 is set to about 30 mm, and the dimension W1 in the width direction X of the air bladder 922 is set to be about 5 mm smaller than that. Similarly to the cuff 820 shown in FIG. 16, the cuff 920 is connected to the blood pressure monitor main body 10 via a flexible elongated air tube 10B, whereby the blood pressure monitor (indicated by reference numeral 9000) is formed.

As shown approximately in FIG. 16, the commercially-available wrist-type blood pressure monitor (standard blood pressure monitor) 6310 includes a cuff 6320 that is wrapped around the wrist 90, and a main body 10 that is integrally attached to the cuff 6320 and has an element for blood pressure measurement built in. The cuff 6320 corresponds to the cuff 920 of the second comparative example in which the dimension W in the width direction X is set to about 52 mm and the dimension W1 in the width direction X of the air bladder is set to about 5 mm smaller than that.

As shown in FIG. 16, blood pressure measurement for verification is performed by attaching the standard blood pressure monitor 6310 (cuff 6320) to the right wrist 90R of the measurement subject and successively attaching the blood pressure monitor 8000 including the cuff 820 of the first comparative example, the blood pressure monitor 9000 including the cuff 920 of the second comparative example, and the blood pressure monitor 1 including the cuff 20 of the first embodiment to the left wrist 90L of the measurement subject. Specifically, the measured values obtained by the standard blood pressure monitor 6310 attached to the right wrist 90R and the measured values obtained by the blood pressure monitor 8000 including the cuff 820 of the first comparative example attached to the left wrist 90L were simultaneously measured repeatedly 5 times. Also, the measured values obtained by the standard blood pressure monitor 6310 attached to the right wrist 90R and the measured values obtained by the blood pressure monitor 9000 including the cuff 920 of the second comparative example attached to the left wrist 90L were simultaneously measured repeatedly 5 times. Also, the measured values obtained by the standard blood pressure monitor 6310 attached to the right wrist 90R and the measured values obtained by the blood pressure monitor 1 including the cuff 20 of the first embodiment attached to the left wrist 90L were simultaneously measured repeatedly 5 times.

Figure 17:
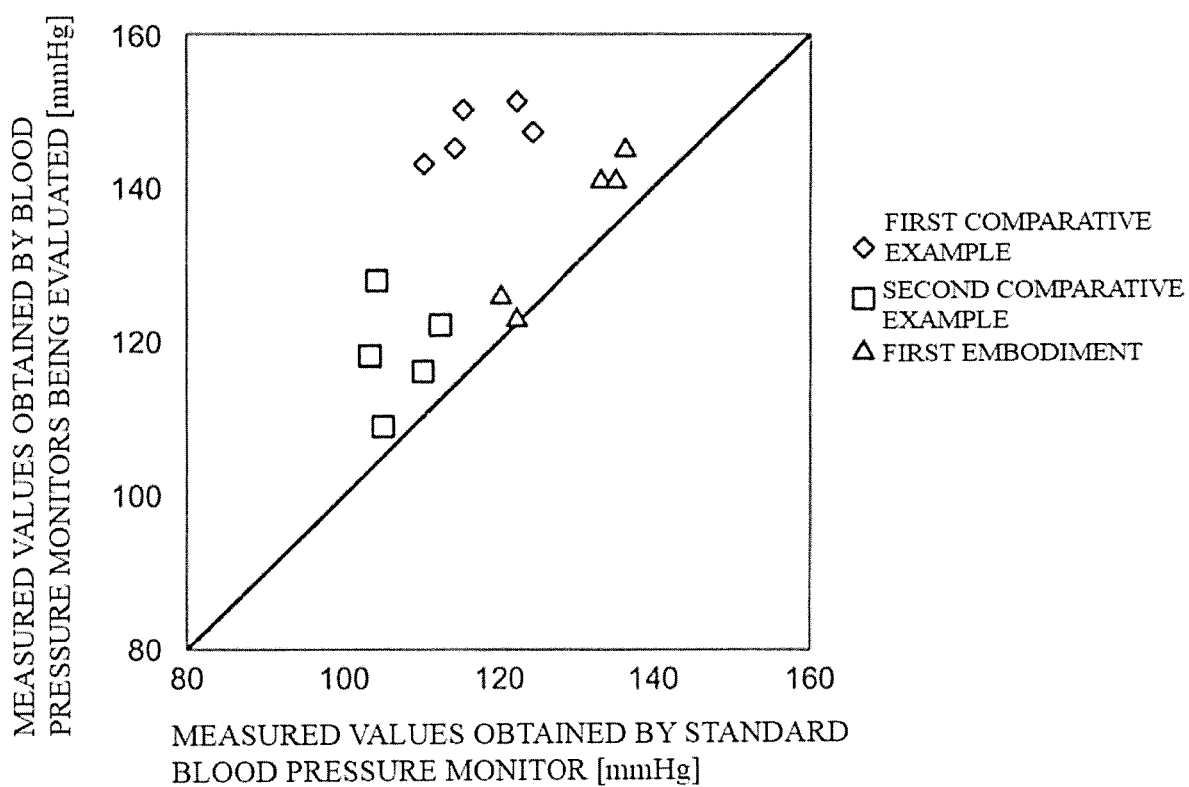
FIG. 17 is a scatter diagram showing the result of comparing measured values obtained by a standard blood pressure monitor and measured values obtained by a blood pressure monitor that is to be evaluated.

FIG. 17 shows a scatter diagram obtained when the measured values (systolic blood pressure) obtained by the standard blood pressure monitor 6310 are set on the horizontal axis and the measured values (systolic blood pressure) obtained by the blood pressure monitors 8000, 9000, and 1 that are being evaluated are set on the vertical axis.

As can be understood from FIG. 17, the measured values (reference sign ◇) obtained by the blood pressure monitor 8000 including the cuff 820 of the first comparative example are much higher than the measured values obtained by the standard blood pressure monitor 6310. The differences obtained by subtracting the measured values (simultaneously measured) obtained by the blood pressure monitor 6310 from the measured values obtained by the blood pressure monitor 8000 were 30.2 mmHg on average, 35 mmHg maximum, and 23 mmHg minimum. This is thought to be because the compression is insufficient since the dimension W in the width direction X of the cuff 820 is set to be about 30 mm, which is smaller than the width direction dimension (52 mm) of the cuff 6320 of the standard blood pressure monitor 6310.

Although the measured values (reference sign □) obtained by the blood pressure monitor 9000 including the cuff 920 of the second embodiment are improved compared to those of the first comparative example, they vary significantly and are still higher than the measured values obtained by the standard blood pressure monitor 6310. The differences obtained by subtracting the measured values (simultaneously measured) obtained by the blood pressure monitor 6310 from the measured values obtained by the blood pressure monitor 9000 were 11.8 mmHg on average, 24 mmHg maximum, and 4 mmHg minimum.

The measured values (reference sign △) obtained by the blood pressure monitor 1 including the cuff 20 of the first embodiment vary less than those of the second comparative example and are further improved. The differences obtained by subtracting the measured values (those measured at the same time) obtained by the blood pressure monitor 6310 from the measured values obtained by the blood pressure monitor 1 were 6.0 mmHg on average, 9 mmHg maximum, and 1 mmHg minimum.

Thus, it can be verified that it is possible to bring the measured values for the blood pressure close to the true values and the measurement accuracy can be increased according to the blood pressure monitor 1 including the cuff 20 of the first embodiment.

Third Embodiment; Blood Pressure Measurement Method

In the above-described embodiments, according to a distinctive configuration of the blood pressure measurement cuff, during inflation for blood pressure measurement, the stroke amount by which the second fluid bladder region swells is larger in the thickness direction than the stroke amount by which the first fluid bladder region swells. However, there is no limitation to this. For example, the method of inflation may be controlled such that the stroke amount by which the air bladder 26 swells is larger in the thickness direction than the stroke amount by which the air bladder 25 swells during inflation for blood pressure measurement, while a known blood pressure measurement cuff 120 (includes the air bladder 25 serving as the first fluid bladder corresponding to the half surface 90a on the palm side of the wrist 90 and the air bladder 26 serving as the second fluid bladder corresponding to the half surface 90b on the back side) shown in FIG. 20, for example, is used.

Figure 20:
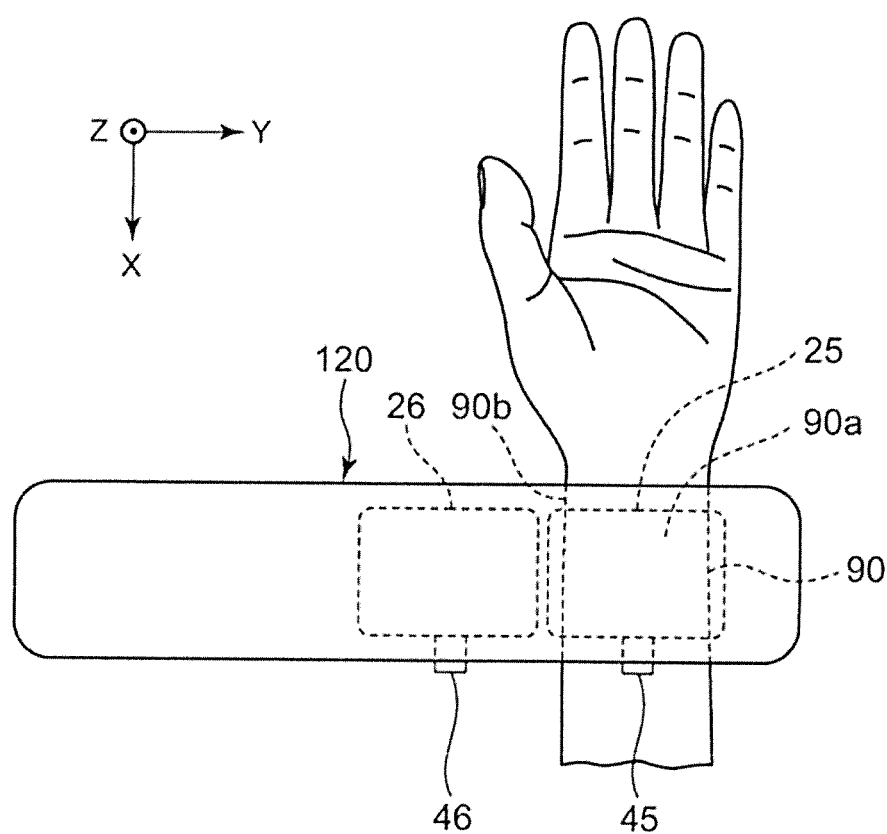
FIG. 20 is a diagram showing a configuration of a cuff to be used to carry out a blood pressure measurement method according to an embodiment of the present invention.

Note that as shown in FIG. 20 (planar layout in a view of a surface corresponding to the outer circumferential side in the unrolled state of the cuff 120), nipples 45 and 46 for receiving a supply of fluid are provided on air bladders 25 and 26 in the cuff 120. For the sake of simplicity, illustration of the planar fastener 70 and the ring 80 for folding over is not included in FIG. 20.

Figure 21:
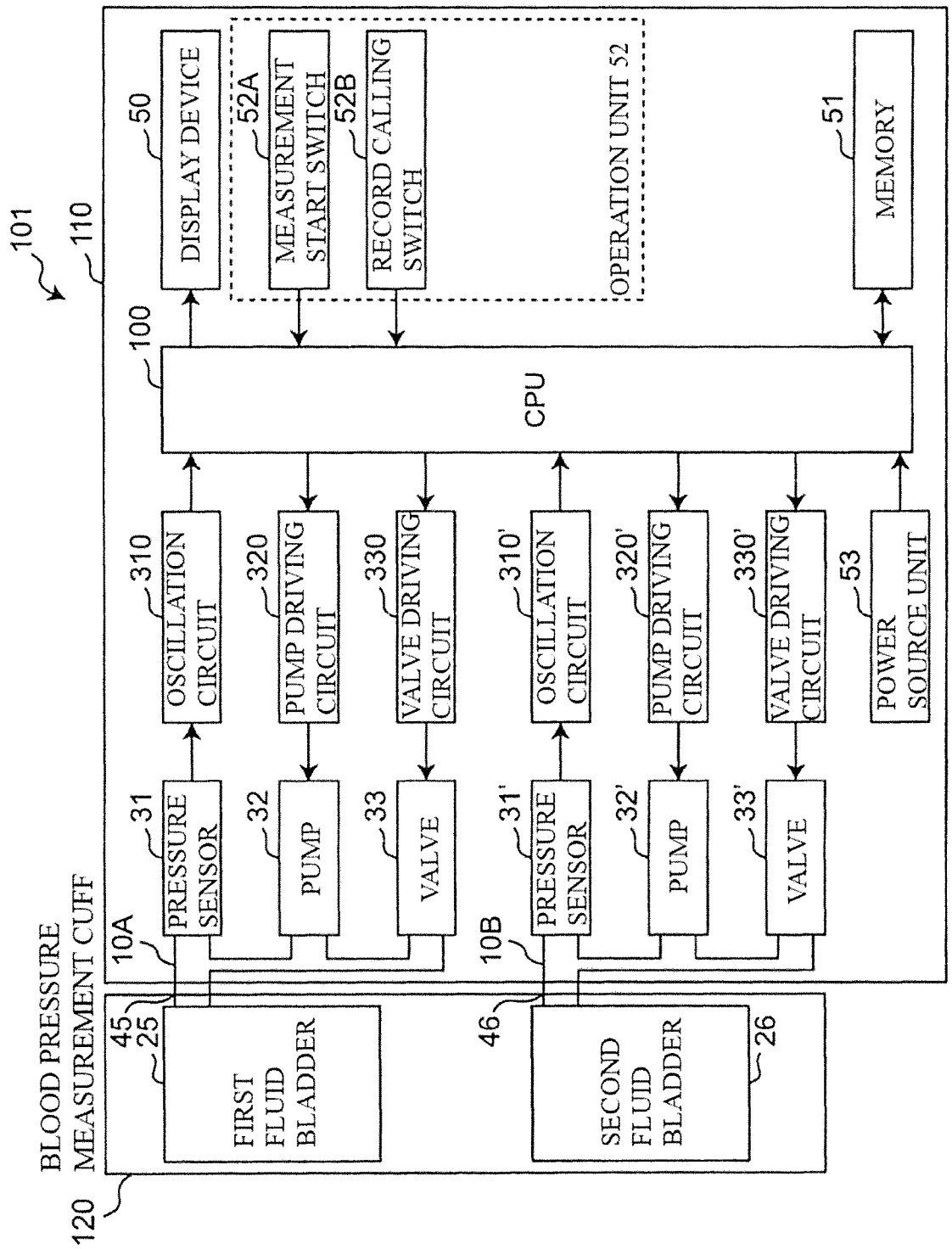
FIG. 21 is a diagram showing a schematic block configuration of a blood pressure monitor to be used to carry out the blood pressure measurement method.

FIG. 21 shows a schematic block configuration of a blood pressure monitor 101 including the cuff 120. Constituent elements that are the same as the constituent elements in FIG. 3 are denoted by the same reference numerals, and detailed description thereof is omitted as appropriate. The blood pressure monitor 101 corresponds to the blood pressure monitor 1 shown in FIG. 3 in which the pressure sensor 31', the pump 32', the valve 33', the oscillation circuit 310', the pump driving circuit 320', the valve driving circuit 330', and the air tube 10B for controlling the pressure of the air bladder 26 have been added to the main body 110. The functions of the elements 31', 32', 33', 310', 320', 330', and 10B are similar to the functions of the elements 31, 32, 33, 310, 320, 330, and 10A for controlling the pressure of the air bladder 25.

Figure 24:
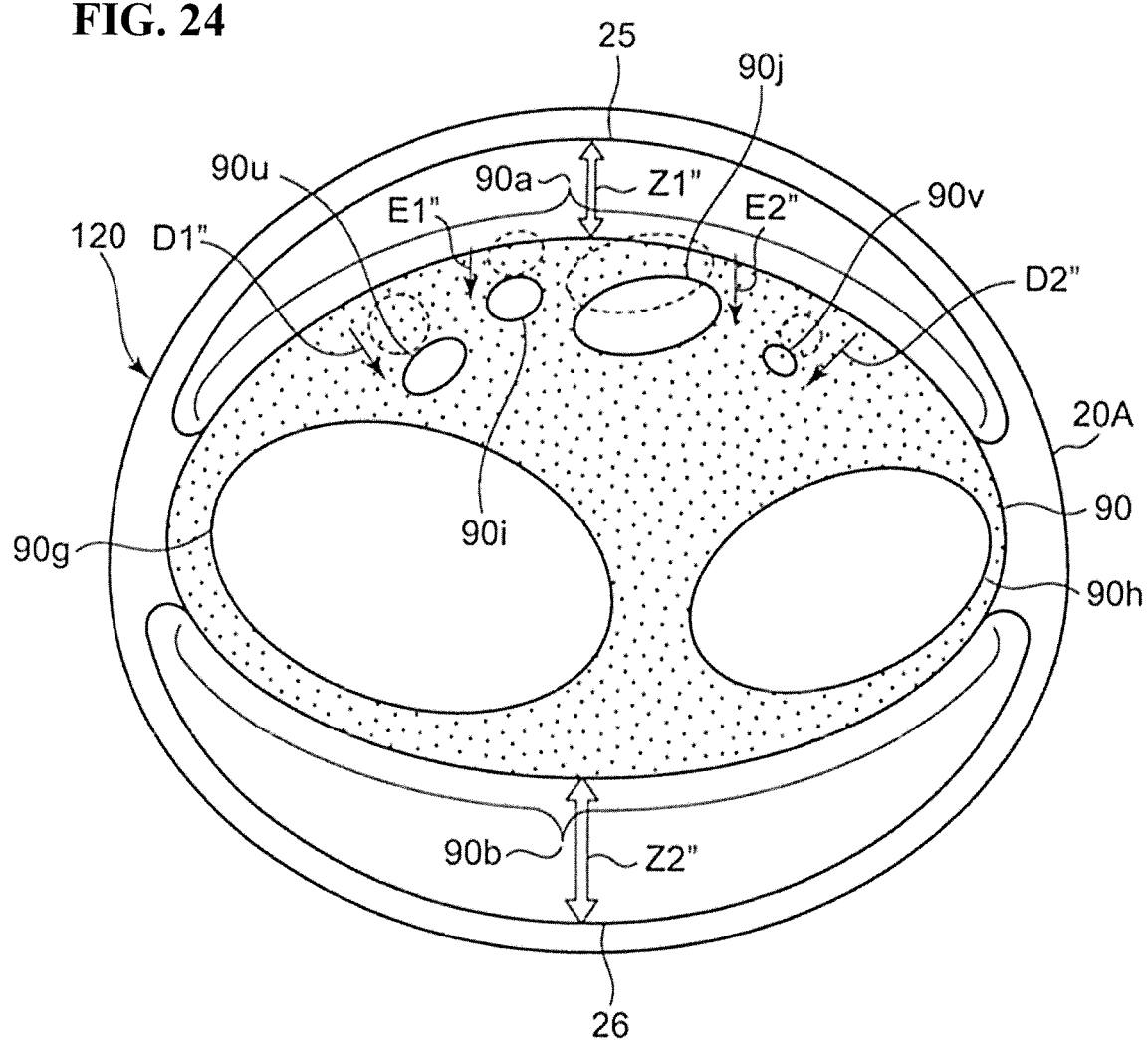
FIG. 24 is a diagram showing a cross section taken orthogonally to the wrist, in a state in which the cuff shown in FIG. 20 is attached to the wrist.

FIG. 24 shows a cross section taken orthogonally to the wrist 90 with the cuff 120 attached to the wrist 90. The air bladder 25 corresponds to the half surface (half surface on the upper side in FIG. 24) 90a on the palm side in the state in which the cuff 120 is attached to the wrist 90. On the other hand, the air bladder 26 corresponds to the half surface (in FIG. 24, the half surface on the lower side) 90b on the back side. Note that in FIG. 24, for the sake of simplicity, illustration of the inner cloth 20B is not included.

Figure 22:
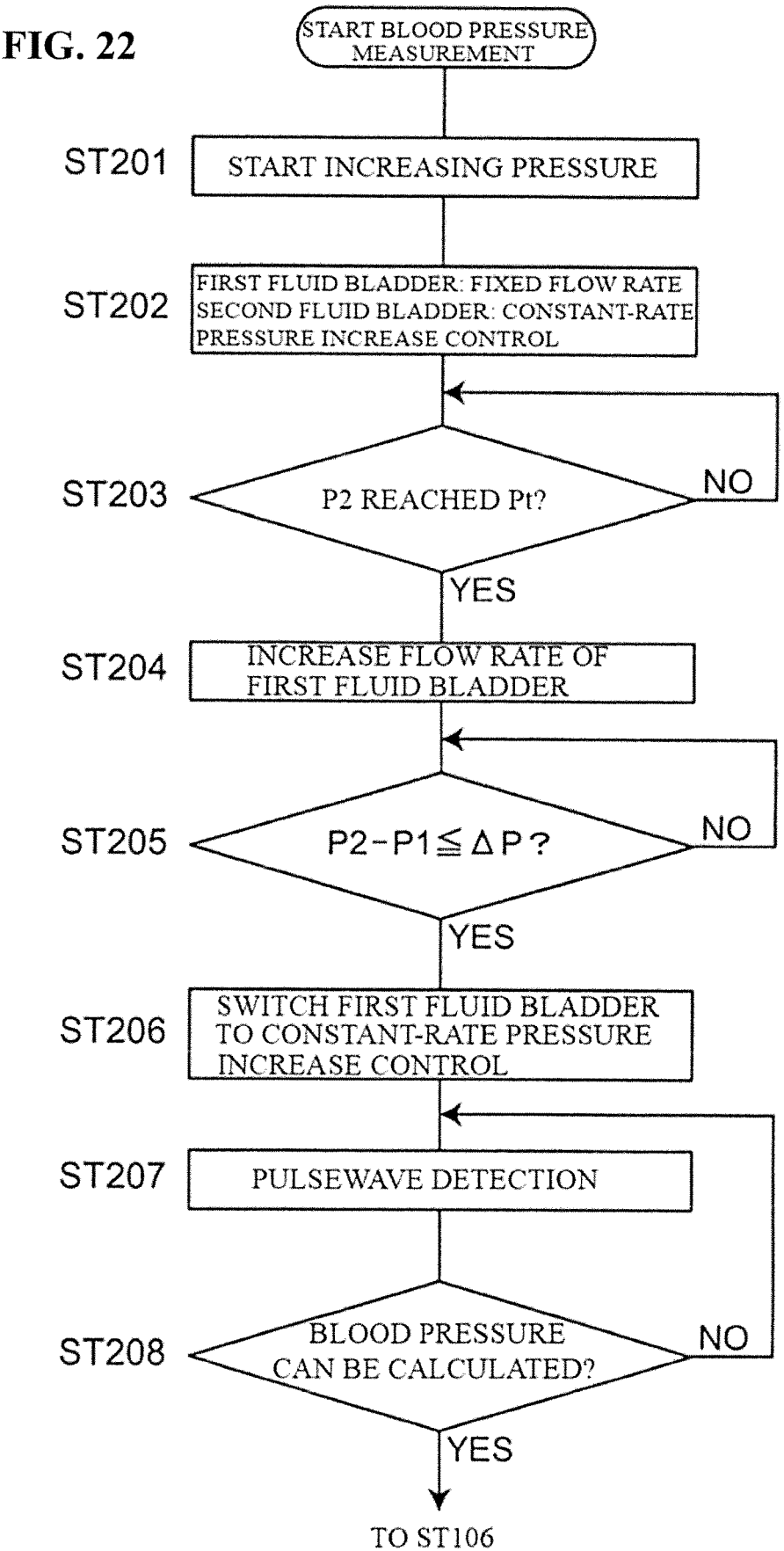
FIG. 22 is a diagram showing a control flow for carrying out the blood pressure measurement method.

With this blood pressure measurement method, the blood pressure values of the measurement subject are measured by the CPU 100 in the blood pressure monitor main body 110 using an oscillometric method in accordance with the flow shown in FIG. 22.

Specifically, when the measurement start switch 52A is pressed (turned on), the blood pressure monitor 101 starts blood pressure measurement as shown in FIG. 22. When blood pressure measurement is started, the CPU 100 initializes a memory region for processing and outputs a control signal to the valve driving circuits 330 and 330'. The valve driving circuits 330 and 330' discharge the air in the air bladders 25 and 26 of the cuff 120 by opening the valves 33 and 33' based on the control signal. Next, control for adjusting the pressure sensors 31 and 31' to 0 mmHg is performed.

Figure 23:
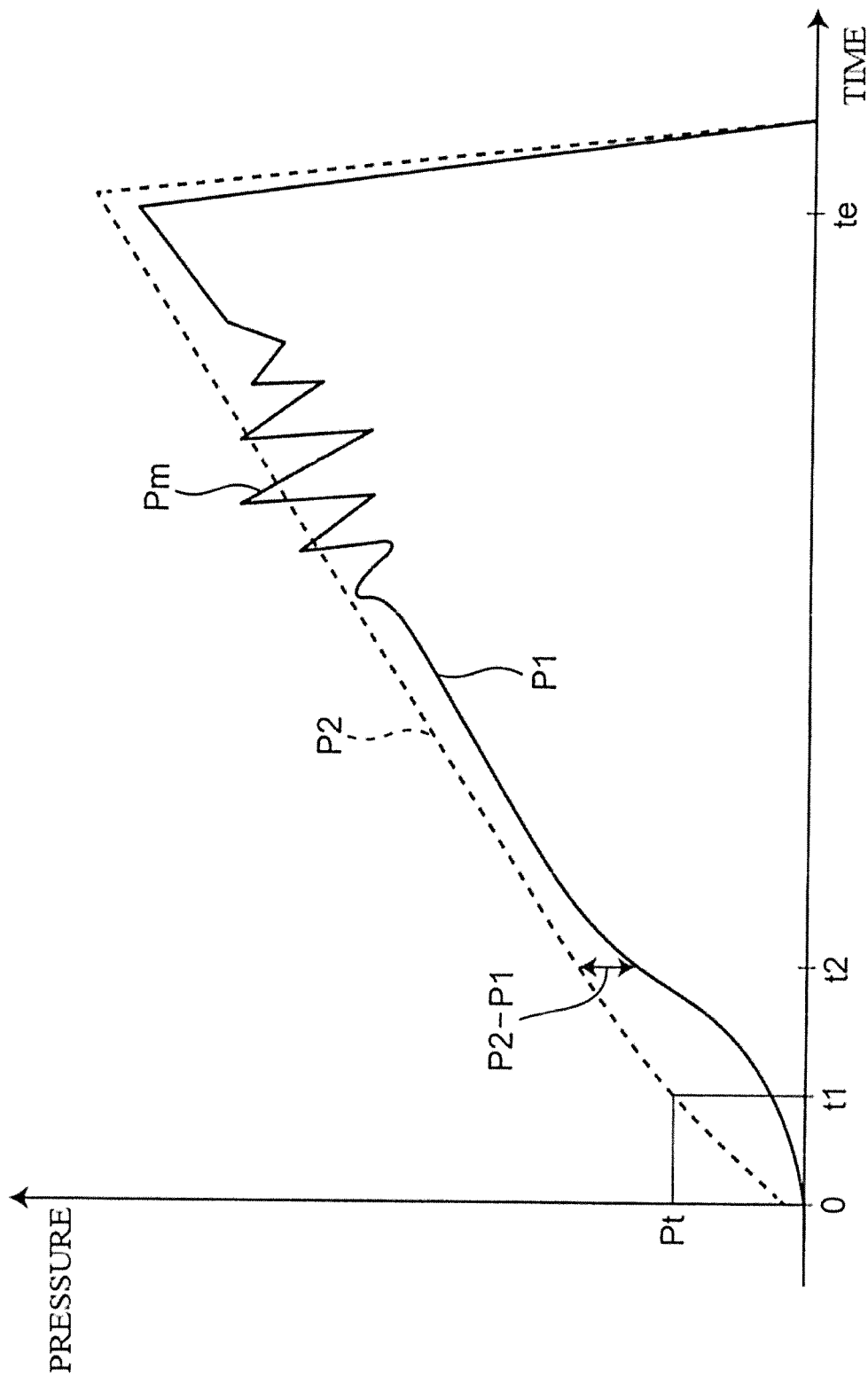
FIG. 23 is a graph showing a method of inflating the first and second fluid bladders of the cuff using the blood pressure measurement method.

Upon starting the blood pressure measurement, first, the CPU 100 closes the valves 33 and 33' via the valve drive circuits 330 and 330', and thereafter drives the pumps 32 and 32' via the pump driving circuits 320 and 320' so as to start control for inflating the air bladders 25 and 26 (step ST201). Here, the supply of air to the air bladder 25 serving as the first fluid bladder is set to a fixed flow rate, such as 10 sccm (standard cc/min), for example. On the other hand, the supply of air to the air bladder 26 serving as the second fluid bladder is subjected to inflation control at a constant rate, such as 5.5 mmHg/sec, for example (step ST202). Accordingly, as indicated in the period from time 0 to t1 in FIG. 23, first, more fluid is supplied to the air bladder 26 than to the air bladder 25, and the pressure P2 (indicated by the broken line in FIG. 23) of the air bladder 26 is raised, or in other words, increased more quickly than the pressure P1 (indicated by the solid line in FIG. 23) of the air bladder 25 is. As a result, as shown in FIG. 24, the stroke amount Z2" by which the air bladder 26 serving as the second air bladder swells is larger in the thickness direction Z of the cuff than the stroke amount Z1" by which the air bladder 25 serving as the first bladder swells.

Next, the CPU 100 determines whether or not the pressure P2 of the air bladder 26 has reached a predetermined pressure Pt (in this example, Pt=20 mmHg) based on the output of the pressure sensor 31' (step ST203 in FIG. 22). In this example, the pressure P2 of the air bladder 26 reaches the pressure Pt at time t1. This means that the air bladder 26 has completed a certain degree of swelling earlier than the air bladder 25. Upon doing so, the CPU 100 increases the supply of air to the air bladder 25 serving as the first air bladder to a flow rate in the range of 20 sccm to 30 sccm, for example, with the fixed flow rate as-is (step ST204 in FIG. 22). Accordingly, as indicated in the period between time t1 and t2 in FIG. 23, the rate of increase of the pressure P1 of the air bladder 25 increases so that the pressure P1 of the air bladder 25 approaches the pressure P2 of the air bladder 26.

Next, the CPU 100 determines whether or not the difference (P2-P1) between the pressure P2 of the air bladder 26 and the pressure P1 of the air bladder 25 is less than or equal to a predetermined threshold (denoted by $\Delta P$) based on the outputs of the pressure sensors 31 and 31' (step ST205 of FIG. 22). The value of $\Delta P$ is set to several mmHg, for example, based on experience, such that P2 and P1 do not invert. In this example, the difference (P2-P1) is less than or equal to the threshold $\Delta P$ at time t2. Upon doing so, the CPU 100 switches the supply of air to the air bladder 25 serving as the first fluid bladder to inflation control at a constant rate such as 5.5 mmHg/sec in this example (step ST206 in FIG. 22). The pressure increase rate is equal to the pressure increase rate of the air bladder 26 serving as the second fluid bladder. Accordingly, the air bladders 25 and 26 are gradually inflated as indicated in the period from time t2 to te in FIG. 23 while ensuring a state in which the stroke amount Z2" by which the air bladder 26 serving as the second fluid bladder swells is larger in the thickness direction Z of the cuff than the stroke amount Z1" by which the air bladder 25 serving as the first fluid bladder swells.

In this example, in the process of inflation, the CPU 100 detects a pulsewave signal Pm (varying component of the pressure P1) based on the output of the pressure sensor 31 and calculates the blood pressure values (systolic blood pressure and diastolic blood pressure) by applying a known algorithm according to the oscillometric method (steps ST207 and ST208 in FIG. 22). Note that blood pressure measurement may be performed in the process of deflation at a pressure reduction rate that is mutually equal to that after the inflation process.

When the blood pressure values are calculated and decided (YES in step ST208), the CPU 100 performs control for displaying the calculated pressure values on the display device 50 (step ST106) and storing the blood pressure values in the memory 51 (step ST107), similarly to the description given with reference to FIG. 3.

When measurement ends (time to in FIG. 23), the CPU 100 performs control for opening the valves 33 and 33' via the valve driving circuits 330 and 330' and discharging the air in the air bladders 25 and 26 of the cuffs 120 (step ST108 in FIG. 3).

In the case of performing blood pressure measurement in this way, as shown in FIG. 24, blood pressure measurement can be performed while ensuring a state in which the stroke amount Z2" by which the air bladder 26 serving as the first air bladder swells is larger in the thickness direction Z of the cuff than the stroke amount Z1" by which the air bladder 25 serving as the first bladder swells. Accordingly, during blood pressure measurement, the distance (denoted by the arrows D1" and D2") by which the arteries 90$u$ and 90$v$ in the wrist 90 serving as the measurement site withdraw due to being pressed by the fluid bladder 25 decreases, and the extra inflation amount for pressing the arteries 90$u$ and 90$v$ decreases. Specifically, the air bladder 25 enters a state of compressing the entire region of the half surface 90$a$ on the palm side including the tendons 90$i$ and 90$j$ in a dispersed manner as indicated by the arrows E1", E2", D1", and D2", rather than swelling toward the soft tissues between the palmaris longus tendon 90$i$ and the radius 90$g$ and between the flexor digitorum superficialis tendon 90$j$ and the ulna 90$h$. Accordingly, the distances D1" and D2" by which the arteries 90$u$ and 90$v$ withdraw decreases, and the extra pressure amount for pressing the arteries 90$u$ and 90$v$ decreases. As a result, the measured values for blood pressure measured through inflation using the cuff 120 can be brought closer to the true values and measurement accuracy can be increased.

Modified Example of Blood Pressure Measurement Method

Figure 25:
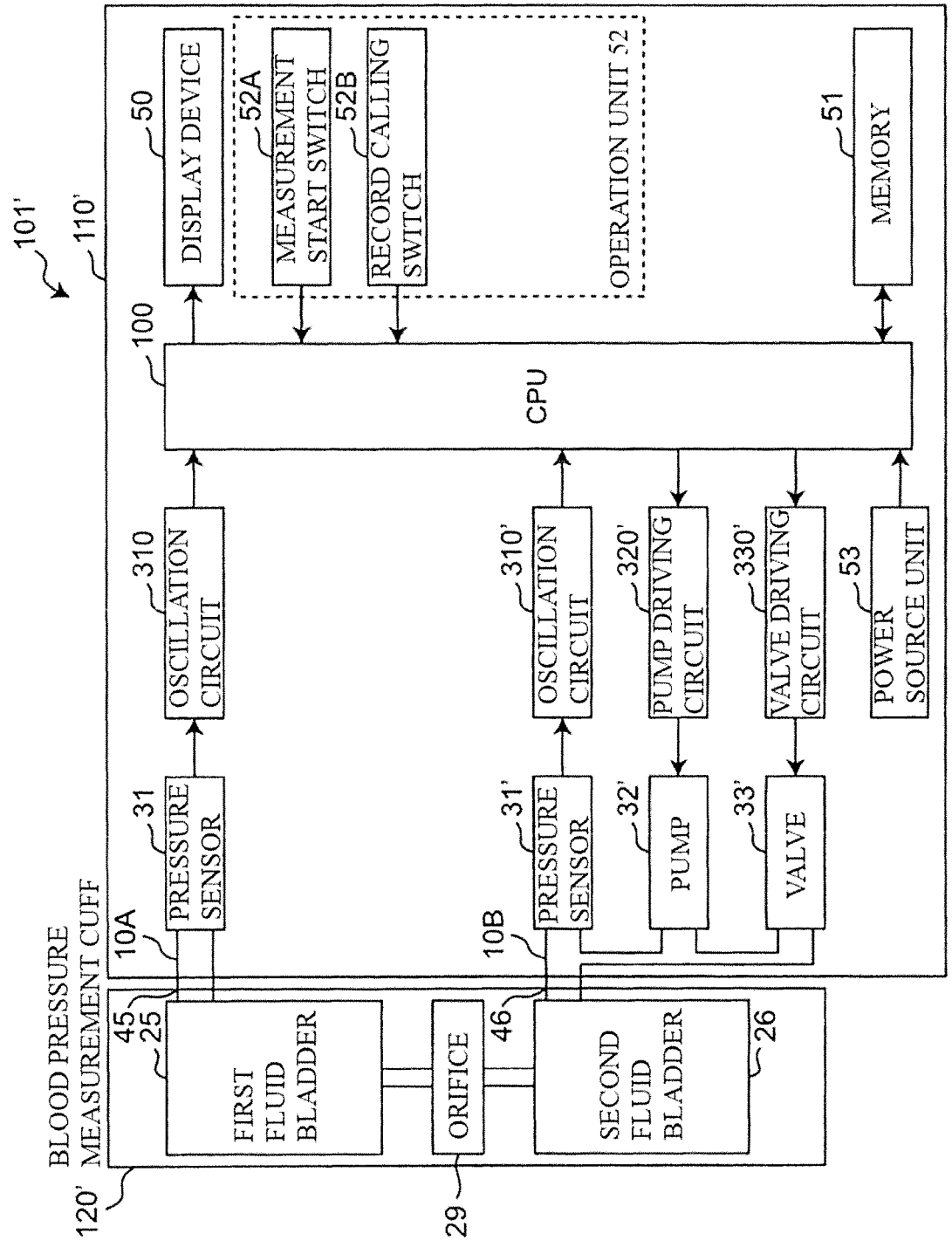
FIG. 25 is a diagram showing another block configuration of a blood pressure monitor to be used to carry out the blood pressure measurement method.
Figure 26A:
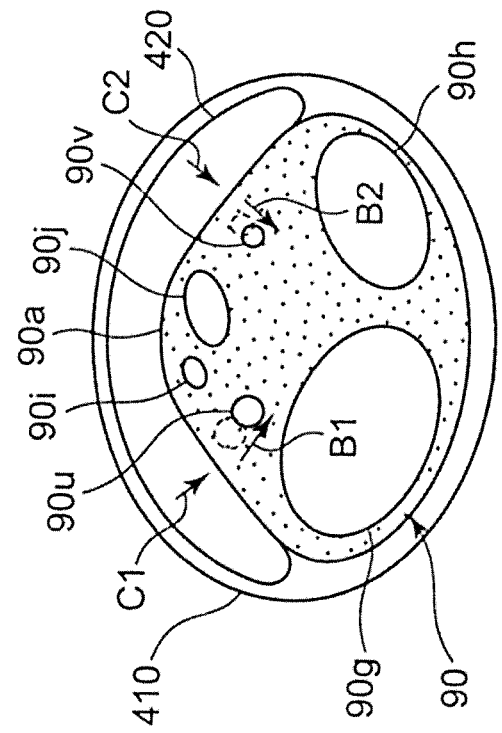
FIGS. 26(A) and 26(B) are diagrams illustrating an object according to one or more embodiments of the present invention.
Figure 26B:
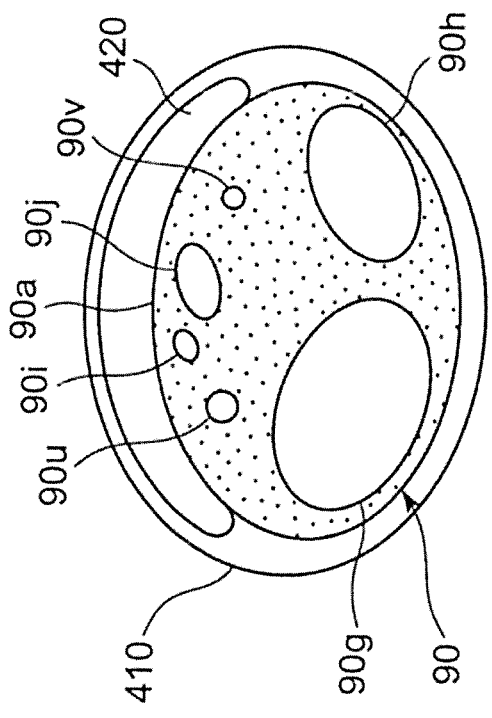

The above-described blood pressure measurement method can also be executed using the blood pressure monitor 101' including the cuff 120' shown in FIG. 25.

With the cuff 120' shown in FIG. 25, the air bladder 25 serving as the first fluid bladder and the air bladder 26 serving as the second fluid bladder are coupled such that air serving as the fluid can flow therethrough via an orifice 29 indicating a fluid resistance. With the main body 110' of the blood pressure monitor 101', the elements 32, 33, 320, and 330 for controlling the pressure of the air bladder 25 are omitted in comparison to the block diagram shown in FIG. 21.

With the blood pressure monitor 101', the supply of air to the air bladder 26 serving as the second fluid bladder is subjected to inflation control at a constant rate by the CPU 100 during inflation for blood pressure measurement. The air bladder 25 serving as the first fluid bladder receives a supply of air from the air bladder 26 via the orifice 29. Accordingly, the pressure P1 of the air bladder 25 becomes larger than the pressure P2 of the air bladder 26 later because of the fluid resistance indicated by the orifice 29. As a result, the pressure P1 of the air bladder 25 and the pressure P2 of the air bladder 26 change approximately similarly to those shown in FIG. 23. Accordingly, similarly to FIG. 24, blood pressure measurement can be performed while ensuring a state in which the stroke amount Z2" by which the air bladder 26 serving as the second fluid bladder swells is larger in the thickness direction Z of the cuff than the stroke amount Z1" by which the air bladder 25 serving as the first fluid bladder swells. Accordingly, the measurement accuracy can be increased.

With the blood pressure monitor 101', the elements 32, 33, 320, and 330 for controlling the pressure of the air bladder 25 can be omitted, and thus the configuration of the main body 110' can be simplified.

With the above-described embodiments, the measurement site was the wrist 90, but there is no limitation to this. The measurement site may be another site, such as an upper arm.

Also, in the above-described embodiments, the blood pressure measurement cuff was of a type that is worn around the measurement site by being folded over through a ring, but there is no limitation to this. The blood pressure measurement cuff may be of a type that is worn by being wrapped around a measurement site in one direction in a spiral shape.

Also, in the above-described embodiments, the blood pressure measurement cuff was constituted by containing an air bladder serving as a fluid bladder in a band-shaped member. However, there is no limitation to this. The fluid bladder is made of elastomer, for example, and the fluid bladder may be constituted by a blood pressure measurement cuff.

Also, the fluid was air, but there is no limitation to this. The fluid may be a fluid that can inflate and deflate the fluid bladder, such as nitrogen.

While the present invention has been described with reference to specific embodiments, the present invention is not limited to these embodiments, and many modifications can be made without departing from the technical idea of the disclosed invention. The multiple above-described embodiments can be achieved independently or used in combination with each other. Also, although the various characteristics of the different embodiments can be achieved independently, it is also possible to combine characteristics of the different embodiments.

REFERENCE NUMERALS LIST 1, 101, 101' Blood pressure monitor
10, 110, 110' Main body
20, 20', 20", 120, 120' Cuff
22, 22', 22", 25, 26 Air bladder
23 Parent bladder
24 Child bladder
A1, A1', A1" First fluid bladder region
A2, A2', A2" Second fluid bladder region
45, 46 Nipple

The invention claimed is:

1. A blood pressure measurement method comprising attaching a band-shaped measurement cuff such that it wraps around a substantially rod-shaped measurement site, wherein the cuff comprises:
a first fluid bladder that swells due to receiving a supply of fluid and is adapted to be arranged only at a portion of an outer circumferential surface of the measurement site that corresponds to a first half surface where an artery is, in a lengthwise direction of the cuff; and
a second fluid bladder that swells due to receiving a supply of fluid and is adapted to be arranged only at a portion of the outer circumferential surface of the measurement site that corresponds to a second half surface opposite to the first half surface, in a lengthwise direction of the cuff, such that the first fluid bladder region and the second fluid bladder region do not overlap along the lengthwise direction of the cuff,
wherein, during inflation for blood pressure measurement, the pressure of the second fluid bladder is made larger than the pressure of the first fluid bladder by supplying more fluid to the second fluid bladder than to the first fluid bladder such that the stroke amount by which the second fluid bladder swells is larger in the thickness direction of the cuff than the stroke amount by which the first fluid bladder swells, and wherein after the stroke amount by which the second fluid bladder swells is made larger in the thickness direction than the stroke amount by which the first fluid bladder swells, the first fluid bladder and the second fluid bladder are inflated at pressure increase rates that are equal to each other, and in the process of inflating, or in the process of deflating at pressure reduction rates that are equal to each other after the process of inflating, blood pressure measurement is performed.

* * * * *